(12) United States Patent
Sculli et al.

(10) Patent No.: US 10,922,894 B2
(45) Date of Patent: Feb. 16, 2021

(54) METHODOLOGY AND SYSTEM FOR MAPPING A VIRTUAL HUMAN BODY

(71) Applicant: Biodigital, Inc., New York, NY (US)

(72) Inventors: Frank Sculli, Brooklyn, NY (US); Lauren Slomovich, North Woodmere, NY (US); Tarek Helmy Sherif, New York, NY (US); John J. Qualter, III, Fair Haven, NJ (US); Aaron Oliker, Oradell, NJ (US)

(73) Assignee: Biodigital, Inc., New York, NY (US)

( * ) Notice: Subject to any disclaimer, the term of this patent is extended or adjusted under 35 U.S.C. 154(b) by 0 days.

(21) Appl. No.: 15/174,700

(22) Filed: Jun. 6, 2016

(65) Prior Publication Data

US 2017/0352194 A1 Dec. 7, 2017

(51) Int. Cl.
| | | |
|---|---|---|
| *G06T 19/20* | (2011.01) | |
| *G06T 9/00* | (2006.01) | |
| *G06T 13/40* | (2011.01) | |
| *G16H 40/63* | (2018.01) | |
| *G16H 50/50* | (2018.01) | |
| *G16H 30/40* | (2018.01) | |

(52) U.S. Cl.
CPC .............. *G06T 19/20* (2013.01); *G06T 9/00* (2013.01); *G06T 13/40* (2013.01); *G16H 30/40* (2018.01); *G16H 40/63* (2018.01); *G16H 50/50* (2018.01); *G06T 2207/30196* (2013.01); *G06T 2210/41* (2013.01)

(58) Field of Classification Search
CPC ...... G09B 23/28; G09B 23/285; G09B 23/30; G09B 19/003; G09B 23/286; G09B 9/00; G06F 19/321; G06F 19/3437; G06F 3/04815; G06F 17/241; G06F 3/04842; G06T 19/006; G06T 19/00; G06T 19/20; G06T 11/60; G06T 13/20; G06T 15/00
See application file for complete search history.

(56) References Cited

U.S. PATENT DOCUMENTS

| | | | | |
|---|---|---|---|---|
| 6,429,431 | B1* | 8/2002 | Wilk | ........ G01T 1/161 |
| | | | | 250/363.01 |
| 6,608,628 | B1* | 8/2003 | Ross | ........ G06T 17/20 |
| | | | | 345/619 |

(Continued)

*Primary Examiner* — Sultana M Zalalee
(74) *Attorney, Agent, or Firm* — Foley Hoag LLP; Stephen J. Kenny

(57) ABSTRACT

Described herein are embodiments of a system for presenting a computer-generated, three-dimensional visualization of anatomy. In some embodiments, the system may enable adjustments to be made to a base anatomical visualization to enable an adjusted visualization to be generated and output by the computing device. In some such embodiments, a specification of such an adjustment may include an identification of one or more anatomical features to which the adjustment corresponds and which are to be visualized with the adjustment. The visualization may correspond, for example, to a medical condition to be visualized. The medical condition may be mapped to one or more data objects of a visualization and the visualization may be adjusted based on the specification. For example, geometric information on anatomical feature may be adjusted to specify a different geometry, to indicate an impact of the medical condition on the anatomical feature.

33 Claims, 17 Drawing Sheets

(56) References Cited

U.S. PATENT DOCUMENTS

| | | | | |
|---|---|---|---|---|
| 6,628,286 B1* | 9/2003 | Comair | | G06T 13/40 345/427 |
| 9,262,862 B2* | 2/2016 | Tsai | | G06T 7/596 |
| 2003/0228040 A1* | 12/2003 | Oosawa | | G06T 7/0012 382/128 |
| 2007/0038223 A1* | 2/2007 | Marquart | | A61B 34/20 606/86 R |
| 2007/0285424 A1* | 12/2007 | Cheng | | G06T 19/00 345/427 |
| 2009/0153552 A1* | 6/2009 | Fidaleo | | G06Q 30/02 345/419 |
| 2010/0257214 A1* | 10/2010 | Bessette | | G06F 19/322 707/812 |
| 2011/0074777 A1* | 3/2011 | Lima | | G06T 17/10 345/420 |
| 2011/0144806 A1* | 6/2011 | Sandhu | | A61B 34/71 700/264 |
| 2011/0170752 A1* | 7/2011 | Martin | | G09B 23/285 382/128 |
| 2012/0058457 A1* | 3/2012 | Savitsky | | G09B 23/286 434/262 |
| 2012/0159308 A1* | 6/2012 | Tseng | | G06F 9/4443 715/234 |
| 2012/0282583 A1* | 11/2012 | Thaler | | G09B 23/28 434/267 |
| 2013/0159555 A1* | 6/2013 | Rosser | | G06F 3/038 710/5 |
| 2013/0179183 A1* | 7/2013 | Wagner | | G06Q 50/22 705/2 |
| 2013/0211284 A1* | 8/2013 | Berry | | G09B 5/02 600/558 |
| 2014/0067414 A1* | 3/2014 | Choi | | G06Q 50/22 705/2 |
| 2014/0328519 A1* | 11/2014 | Martinetz | | G06T 7/75 382/107 |
| 2016/0217591 A1* | 7/2016 | Krupnik | | G06T 7/60 |
| 2016/0351200 A1* | 12/2016 | Sung | | G10L 15/30 |

* cited by examiner

METHODOLOGY AND SYSTEM FOR MAPPING A VIRTUAL HUMAN BODY

FIELD

Embodiments of the present invention relate to creating three-dimensional visualizations of anatomy, including adjusting base visualizations of the anatomy to, for example, display supplemental content such as from a medical record or to visualize effects of medical conditions.

BACKGROUND

Medical conditions and their impact on anatomy are often explained through text describing the conditions. The text may identify the medical condition as well as explain how an appearance of an anatomical feature may change as a result of the medical condition. In some cases, the text may be accompanied by static, two-dimensional images, such as illustrations/drawings or photographs. The images may be in two parts, such as an image showing a "normal" anatomical feature for comparison with an image showing the anatomical feature affected by the medical condition.

SUMMARY

In one embodiment, there is provided a method of operating a computing system to generate computer-readable data representing a three-dimensional visualization of at least a portion of anatomy of a human body. The method comprises receiving, at the at least one computing device, a specification of an adjustment to be made to a base three-dimensional visualization of the at least the portion of the anatomy of the human body. The specification of the adjustment comprises an identification of the adjustment to make and an indication of at least one anatomical feature of the human body to which the adjustment relates. The method further comprises mapping, with at least one processor of the at least one computing device, the indication of the at least one anatomical feature of the human body to at least one object of a hierarchy of objects. Each object of the hierarchy of objects corresponds to one or more anatomical features of the human body and to one or more elements of the base three-dimensional visualization. The method further comprises generating, with at least one processor of the at least one first computing device, an adjusted three-dimensional visualization of the at least the part of the anatomy of the human body by adjusting the one or more elements of the base three-dimensional visualization based at least in part on the adjustment. The one or more portions of the base three-dimensional visualization that are adjusted correspond to the one or more objects that were mapped to the at least one anatomical feature indicated by the specification of the adjustment. The adjusted three-dimensional visualization includes the adjustment at the one or more portions that correspond to the one or more objects.

In another embodiment, there is provided at least one non-transitory computer-readable storage medium having encoded thereon executable instructions that, when executed by the at least one processor, cause the at least one processor to carry out a method of operating a computing system to generate computer-readable data representing a three-dimensional visualization of at least a portion of anatomy of a human body. The method comprises receiving, at the at least one computing device, a specification of an adjustment to be made to a base three-dimensional visualization of the at least the portion of the anatomy of the human body. The specification of the adjustment comprises an identification of the adjustment to make and an indication of at least one anatomical feature of the human body to which the adjustment relates. The method further comprises mapping, with at least one processor of the at least one computing device, the indication of the at least one anatomical feature of the human body to at least one object of a hierarchy of objects. Each object of the hierarchy of objects corresponds to one or more anatomical features of the human body and to one or more elements of the base three-dimensional visualization. The method further comprises generating, with at least one processor of the at least one first computing device, an adjusted three-dimensional visualization of the at least the part of the anatomy of the human body by adjusting the one or more elements of the base three-dimensional visualization based at least in part on the adjustment. The one or more portions of the base three-dimensional visualization that are adjusted correspond to the one or more objects that were mapped to the at least one anatomical feature indicated by the specification of the adjustment. The adjusted three-dimensional visualization includes the adjustment at the one or more portions that correspond to the one or more objects.

In a further embodiment, there is provided an apparatus comprising at least one processor and at least one non-transitory computer-readable storage medium having encoded thereon executable instructions that, when executed by the at least one processor, cause the at least one processor to carry out a method of operating a computing system to generate computer-readable data representing a three-dimensional visualization of at least a portion of anatomy of a human body. The method comprises receiving, at the at least one computing device, a specification of an adjustment to be made to a base three-dimensional visualization of the at least the portion of the anatomy of the human body. The specification of the adjustment comprises an identification of the adjustment to make and an indication of at least one anatomical feature of the human body to which the adjustment relates. The method further comprises mapping, with at least one processor of the at least one computing device, the indication of the at least one anatomical feature of the human body to at least one object of a hierarchy of objects. Each object of the hierarchy of objects corresponds to one or more anatomical features of the human body and to one or more elements of the base three-dimensional visualization. The method further comprises generating, with at least one processor of the at least one first computing device, an adjusted three-dimensional visualization of the at least the part of the anatomy of the human body by adjusting the one or more elements of the base three-dimensional visualization based at least in part on the adjustment. The one or more portions of the base three-dimensional visualization that are adjusted correspond to the one or more objects that were mapped to the at least one anatomical feature indicated by the specification of the adjustment. The adjusted three-dimensional visualization includes the adjustment at the one or more portions that correspond to the one or more objects.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
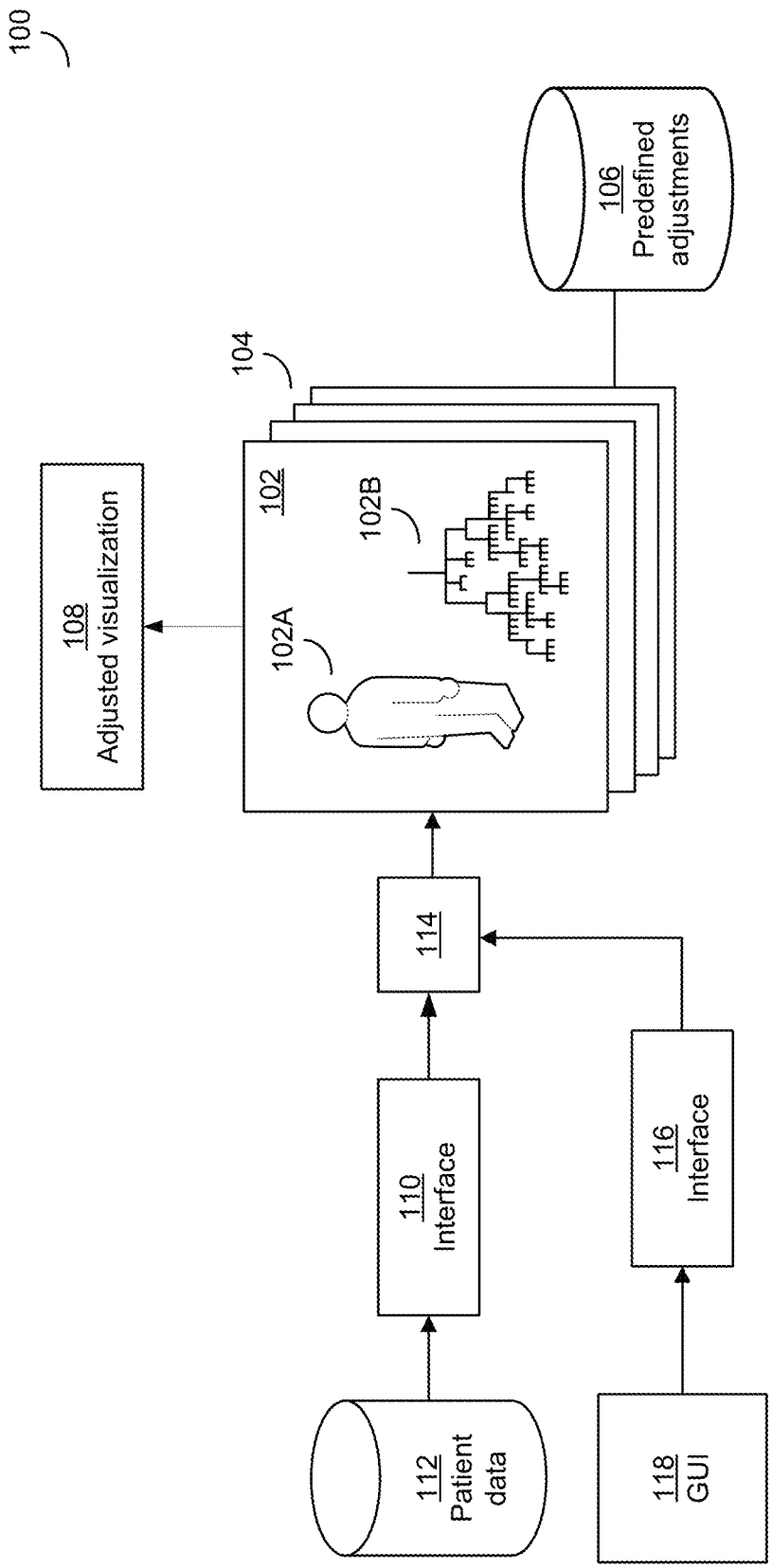
FIG. 1A is a schematic diagram of some exemplary components of a system described herein for visualizing anatomy.

Described herein are embodiments of a system for mapping medical conditions to a virtual human body. Some embodiments may generate a three-dimensional visualization of an entirety or a portion of human anatomy. As part of generating the three-dimensional visualization, input may be received identifying a medical condition affecting the human anatomy. The medical condition may be mapped to one or more anatomical features and the three-dimensional visualization may be adjusted based on the medical condition. For example, geometric information on a manner of visualization an anatomical feature may be adjusted to specify a different geometry, to indicate an impact of the medical condition on the anatomical feature.

In some embodiments, a system may present a computer-generated, three-dimensional visualization of anatomy, such as by generating and displaying, with a computing device, a three-dimensional visualization of a human body or a part of a human body. The three-dimensional visualization may include externally-visible and/or internal anatomical features, including portions of the anatomy like particular regions of a body (e.g., a limb) or particular systems (e.g., muscles, vasculature, etc.). Three-dimensional visualizations of anatomy provide an easy way for people to see and a potentially better way for people to understand anatomical features and interactions between anatomical features. Such visualizations may be fixed or animated to visualize movement of individual anatomical features during a movement of an organism being visualized (e.g., movements of individual leg muscles while walking). The visualizations may also be shown in cross-section or in other ways to assist viewers in seeing and understanding anatomy.

In some embodiments, the system may enable adjustments to be made to the anatomical visualization, to enable an adjusted visualization to be generated and output by the computing device. In some such embodiments, a specification of such an adjustment may include an identification of one or more anatomical features to which the adjustment corresponds and which are to be visualized with the adjustment. The visualization may correspond, for example, to a medical condition to be visualized, such as in the case when the visualization is to correspond to a patient and the patient's medical record indicates that the patient has or may have the medical condition.

In some embodiments, a system may maintain a visualization of anatomy in the form of a hierarchy of objects, where each object corresponds to one or more anatomical features of the anatomy, such as organs or parts of organs of a human body. Some or all of the objects may include information controlling a manner in which the anatomical feature corresponding to the object will be visualized. For example, an object may include geometric information controlling a three-dimensional display of the anatomical feature, and/or geometric information controlling a four-dimensional display in the case that an animation is to be output.

In some embodiments, when a specification of an adjustment to be made is received, the system may determine from the specification anatomical features to which the adjustment relates. The system may map the identification of anatomical features set out in the specification to one or more objects of the hierarchy of objects, where the one or more objects are related to the anatomical features to which the adjustment relates. Based on the specification of the adjustment, one or more edits to the objects and/or the visualization identified by the objects may be made. For example, based on the adjustment, geometric information specified by an object may be edited such that, based on the adjustment, a different geometry is rendered for the visualization. The different geometry may, for example, relate to a medical condition. Accordingly, while the objects may in some embodiments identify geometries for a "normal" visualization of anatomy, edits may be made to these objects to enable different geometries for anatomical variations from normal to be visualized.

In some embodiments, the mapping may permit the anatomical features to which the adjustment relates to be specified using one of a variety of different anatomical coordinate systems. In some such embodiments, the indication of the anatomical feature(s) may describe the anatomical feature(s) using one ontology, and the adjustment facility may map the indication to another, different ontology related to the hierarchy of objects. Medical conditions or other adjustments may thus be specified at varying degrees of specificity and the system may determine which objects are related to the medical condition based on the mapping. In some embodiments, performing the mapping includes determining an ontology used by the specification of the adjustment, and mapping based on that ontology.

Described below are examples of computer-implemented systems for generating, for display, three-dimensional visualizations of anatomy. It should be appreciated that embodiments are not limited to operating in accordance with any of the examples below, as other examples are possible.

FIG. 1 illustrates an example of a computer-implemented visualization system with which some embodiments may operate. Computer-implemented visualization system 100 is adapted to generate a visualization of anatomy, including by generating an adjusted visualization based on a specification of an adjustment to be made to a "base" visualization.

The computer system 100 of FIG. 1A includes a base visualization 102. The base visualization 102 may reflect a visualization of anatomy that can be modified to show variations with respect to that visualization. The base visualization may, for example, reflect a consensus "normal" or "healthy" anatomy for a species. The anatomy may be an entirety of an anatomy for a species, or may be a part of an anatomy. The part of the anatomy may be a particular region of the anatomy, such as a limb, or may be for one or more particular types of tissues of the anatomy, such as one or more systems of organs such as musculature, musculoskeletal system, nervous system, or other types of tissues. As should be appreciated from the discussion below, a visualization that is output may include less than all of the anatomy that is able to be generated based on the information of the visualization 102, such as by "zooming in" on only a portion of the anatomy or selectively rendering parts of the anatomy. Thus, while in some embodiments the information of the base visualization 102 may include information on an entirety of an anatomy of a species, a selective visualization may be rendered that is only of the musculoskeletal anatomy specified by that information or any other part of the anatomy.

The information of the base visualization 102 may be used to render a three-dimensional visualization 102A of the anatomy for output. Thus, the base visualization 102 may include the information that may be used by a 3D rendering engine to create three-dimensional graphics for the anatomy. In the embodiment of FIG. 1A, the information may be included in a hierarchy of data objects 102B.

Each data object of the hierarchy 102B may relate to one or more anatomical features available to be rendered in the visualization 102, which may include organs, tissues, cells, or other structures of an anatomy. The data objects may be organized in the hierarchy 102B in a manner corresponding to an arrangement of anatomical features within an anatomy, or an arrangement of anatomical features in standard anatomical classifications. For example, there may be an object related to the musculoskeletal system, which includes dependent objects that relate to the musculature system and to the skeletal system. The object for the skeletal system may in turn include objects related to different components of the skeletal system, such as bones, joints, and cartilage, and the object for bones may include objects for particular bones (e.g., a femur). Data objects may depend from multiple different objects in some cases. For example, a femur data object may depend from a skeletal system object and/or bone object, but may additionally depend from a "leg" object.

The hierarchy 102B may include connections between data objects at a same level, or connections that do not necessarily indicate a dependency. For example, the hierarchy 102B may include connections between data objects that indicate a relationship between anatomical structures. This may be the case, for example, with an object for a bone and an object for a ligament that attaches to that bone.

In some cases, one or more objects of the hierarchy 102B may not relate to an entirety of an anatomical feature, but may instead correspond to a portion of an anatomical feature. For example, a data object may correspond to a region of an anatomical feature. The region of the anatomical feature may be, for example, a portion of a surface area of the anatomical feature or a part of a volume of the anatomical feature. The region of the anatomical feature may also correspond to a distinct anatomical structure within an anatomical feature, such as a chamber of a heart or gastric glands of the stomach. A data object may also correspond to a particular point on a surface area of or within an anatomical feature.

The hierarchy of data objects 102B may include information on a manner in which to render anatomical features to which the objects correspond. For example, the data object(s) for an anatomical feature may include information on a geometry of the anatomical feature. The information on the geometry may include information on dimensions and shapes of the anatomical feature. Those skilled in the art will appreciate that, for rendering of 3D computer graphics, information on geometry may be stored and used in a variety of ways. Embodiments are not limited to any particular manner of storing information on geometry. As one example, information on geometry may be stored in terms of values or equations that identify dimensions and/or shapes.

In some embodiments, the information on the manner in which to render an anatomical feature may additionally or alternatively include information on an appearance to of the anatomical feature when rendered, or on different appearances to use for different parts of the anatomical feature. For example, if an anatomical feature is to appear with a rough surface or a smooth surface, or with some parts having a rough surface and others a smooth surface, or if one or more colors are to be used, this information may be stored in the data objects. Again, those skilled in the art will appreciate that, for rendering of 3D computer graphics, information on appearance of objects may be stored and used in a variety of ways, and embodiments are not limited to any particular manner of storing information on appearance.

In some embodiments, the information on the manner in which to render an anatomical feature may additionally or alternatively include information on a manner in which the anatomical feature is to be shown moving, either by itself or relative to other anatomical features. This information may be helpful if the anatomical feature is to be animated when rendered. This may be the case when an animated visualization of an organism moving (e.g., walking or running) is to be generated, or when an animated visualization of an anatomical feature (e.g., lungs and/or a heart pumping) is to be generated.

The information on a manner in which to render the anatomical feature may additionally or alternatively include information on a relationship and/or connection to other anatomical features. For example, information on an appearance of the connection between anatomical features, such as a location, size, or type of the connection, may be stored. As another example, information on a manner in which movement of one anatomical feature impacts the other (e.g., how movement of a ligament impacts movement of a bone) may be stored.

Those skilled in the art will appreciate from the foregoing description that there are a variety of ways that the information on the manner in which to render anatomical features may be stored in the data objects. For example, where only a single data object corresponds to an anatomical feature, that single data object may store all of the information on the manner in which to render the anatomical feature. As another example, where multiple data objects correspond to an anatomical feature, or to a collection of anatomical features such as an anatomical system, the information on how to render the feature or collection may be distributed across the multiple data objects. In a case where a data object corresponds to a portion of an anatomical feature, information from multiple data objects may be used to determine a manner in which to render the anatomical feature.

An example was given above of a data object corresponding to one chamber of a heart. In such a case, a data object may correspond to each chamber of a heart, and information from the multiple data objects (for a multi-chambered heart) may be used to render the heart.

Another example was given above of a data object corresponding to a portion of a surface of an anatomical feature, or a point within an anatomical feature. In such a case, there may be other data objects corresponding to other portions of the surface or other points, and the information on a manner in which to render the anatomical feature may be compiled from the multiple data objects.

In some embodiments, as discussed above, the visualization 102 may correspond to a particular state of anatomy, such as a "healthy" or consensus "normal" anatomy for a species like a human. In some embodiments, there may be one or more additional visualizations 104 that correspond to different states of the anatomy for that species. The visualizations 104 may be structured similarly to the foregoing description of the visualization 102, but one or more of the anatomical features that are rendered with a visualization 104 may vary from the anatomical features rendered with the visualization 102 because the visualization 104 corresponds to a different state of the anatomy. The different state of the anatomy may correspond to an injury, procedure (e.g., surgery), disease, genetic mutation, condition, or other factor that causes changes in anatomy, any of which may be generically referred to herein as a "medical condition." For example, a visualization 104 may correspond to obesity, and the anatomical features may be rendered to represent changes to the anatomy resulting from obesity. This may include a larger heart, larger fat deposits, cholesterol deposits within vasculature, inflammation in joints, and/or other anatomical variations that are associated with obesity.

The information for these variations may be stored in one or more data objects of the hierarchy of the visualization 104. For example, information identifying the geometry of a larger heart may be stored in one or more data objects corresponding to a heart, by identifying different values and/or different equations identifying a size or shape of the heart than the values/equations of a corresponding data object in visualization 102. In some cases, there may be additional or fewer data objects than another visualization. For example, when a visualization 102 corresponds to an obese state and vasculature is to be rendered with cholesterol disposed therein, there may be one or more additional data objects for such cholesterol, associated with each vein or artery to be rendered with the cholesterol, as compared to a healthy/normal state of another visualization. Anatomical variations for a visualization 104 may be rendered by rendering anatomical features differently than would be rendered using the visualization 102, such as by using different geometries and/or different appearances in the rendering based on the information stored in data objects of the visualization 104.

Embodiments are not limited to visualizations 102, 104 being associated with a state that has a system-wide effect on multiple parts of an anatomy (e.g., normal state, obese state, etc.). As another example, a visualization 104 may correspond to a stroke, and may represent damage to a brain resulting from a stroke by showing the brain with a different geometry or different appearance. As another example, a visualization 104 may correspond to a surgery, such as a common surgery like a cholecystectomy, and the visualization 104 may render the anatomy different by rendering the anatomy without a gallbladder and with scar tissue in the skin and musculature corresponding to incisions made during the surgery.

As should be appreciated from the foregoing, the visualization system 100 may enable generation of an "adjusted" visualization that has changes with respect to one of the visualizations 102, 104. Various types of adjustments may be made to a visualization in accordance with techniques described herein, some examples of which are described and illustrated below in connection with FIGS. 5A-5F.

For example, an adjustment may be made to reflect an annotation to be added to a visualization. Such an annotation may identify information related to an anatomical feature, such as by identifying the anatomical feature or identifying some additional information with respect to the anatomical feature. Such additional information may be medical information, such as information from a medical dictionary or medical journal, and may be patient-specific information, such as by annotating an anatomical feature with information indicating a complication suffered by a specific patient regarding that anatomical feature. For example, an adjustment may include rendering a visualization with an annotation linked to a heart indicating a patient has a heart murmur. As another example, an adjustment may include rendering a visualization with an annotation linked to skin indicating that there is a growth at a particular location of the skin.

As another example, an adjustment may be made to change a manner in which an anatomical feature is to be rendered, such as by altering a geometry and/or appearance of an anatomical feature. Similarly to the visualizations 104 discussed above, such a change to a manner in which an anatomical feature is to be rendered may reflect a medical condition, such as an injury, procedure, disease, genetic mutation, condition, or other factor that causes changes in anatomy. For example, an adjustment may be made to render a heart with a heart murmur, such as by changing a geometry of the heart, an appearance of the heart, and/or a movement of the heart. in the visualization.

As another example, an adjustment may be made that changes a manner of display of some or all of the visualization. Changing the manner of display may include "zooming in" on a particular part of the visualization, and/or may include omitting some anatomical features from the visualization. Changing the manner of display may further include changing an appearance of one or more anatomical features, such as increasing the transparency with which they are rendered or changing a color with which the anatomical features are rendered.

As with the visualizations 104, the variations may be rendered by rendering anatomical features differently than would be rendered using the visualization 102, such as by using different geometries and/or different appearances in the rendering, and/or by rendering additional or fewer objects (e.g., annotations) or anatomical features in the adjusted visualization. An adjustment may be made by identifying changes to be made to data objects of a visualization, such as by identifying changes to be made to one or more particular data objects of a hierarchy 102B of visualization 102.

For example, information on an adjustment may identify a particular data object related to an anatomical feature and a change to be made to a value or equation stored by that data object that will change a geometry with which the anatomical feature is rendered. The change to be made to the value or equation may include a substitute value or equation, a factor to adjusted the value or equation of the data object (e.g., a scaling factor, a constant factor to be added, etc.) that may be a value or equation, or any other mathematical expression that may adjust a value or equation.

As another example, information on an adjustment may identify that a particular data object of a "normal" visualization 102 is to be replaced with another particular data object from one of the alternate visualizations 104. In some cases, the two data objects (from visualization 102 and from visualization 104) may be corresponding data objects between the two visualization, such as by being located at the same position in the hierarchies of data objects. In such a case, the information identifying the adjustment may identify a data object (e.g., by identifying a and an alternate visualization 104, and identify that In other cases, the data object from visualization 104, that replaces the data object from visualization 102, may be any suitable data object in the visualization 104 at any suitable location in the hierarchy. As such, the data object from a visualization 104 may be within the same anatomical system or relate to the same anatomical feature as the data object being replaced as part of the adjustment.

While in the examples of the preceding two paragraphs, reference was made to a change made to a singular "data object," it should be appreciated that adjustments may be specified for multiple objects, including by referencing multiple objects as a group. For example, where an anatomical feature is related to a hierarchical grouping of data objects, such as a grouping of data objects for a heart or other organ, a change may be specified as relating to the data objects of that group. As a specific example, an adjustment may specify that a collection of data objects for a heart from an alternative visualization 104 be substituted for a collection of data objects for a normal visualization 102. As another specific example, a value or equation may be specified for a change made to a collection of data objects, and adjustments may be made to multiple data objects based on that value/equation.

In some embodiments, the visualization system 100 may include a data store 106 of predefined adjustments. The data store 106 may include a set of adjustments, wherein the information for each adjustment may include an identifier for the adjustment and other information defining or explaining the adjustment (e.g., the name of a surgery or medical condition visualized by the adjustment), information identifying one or more anatomical features impacted by the adjustment and/or identifying one or more data objects (in turn related to one or more anatomical features) that are impacted by the adjustment, and information identifying changes to be made to a base visualization to effect the adjustment. The information identifying the change to be made may include the information, discussed above, identifying a change to a manner in which to render an anatomical feature. This may include information identifying a change to a geometry, appearance, movement, or other characteristics of a manner in which to render an anatomical feature in the visualization, which may include a mathematical expression (e.g., an equation or value) indicating the change.

The visualization system may produce an adjusted visualization through editing a "base" visualization 102, 104 based on one or more adjustments, including one or more of the predefined adjustments 106. The adjusted visualization 108 that is output may include, in some embodiments, graphics data that, when provided to a graphics system of a computing device (e.g., a driver for a graphics card) can be output for display. The adjusted visualization 108 may additionally or alternatively, in some embodiments, include instructions for generating such graphics data, with the instructions set out using any suitable graphics instruction set, including according to a graphics library API (e.g., OpenGL, WebGL, etc.). The adjusted visualization 108 may additionally or alternatively, in some embodiments, include a hierarchy of data objects, similar to the hierarchy 102B described in detail above, that include information on how to render one or more anatomical features.

Adjustments may be made to a visualization 102, 104 based on information received via an interface to the visualization system 100. In the example of FIG. 1A, the visualization system 100 includes two interfaces: a programmatic interface 110 and a user interface 116. The programmatic interface 110 may include an Application Programming Interface (API) to the visualization system 102, which may include an interface for exchanging information via one or more networks, following protocols such as web services protocols.

Programmatic interface 110 may be used, in some embodiments, to receive and process patient data from a data store 112 of patient data, to enable a visualization to be produced based on the patient data 112. The visualization to be produced based on the patient data may represent a state of a patient, or be used to display or explain a medical condition of the patient by annotating a visualization. When the patient data is provided to the visualization system 100 via the interface 110, the patient data may be interpreted via an interpreter 114 to determine an adjustment requested, one or more anatomical features to which the adjustment relates, and a manner in which to render the adjustment. This may include, for example, mapping an identifier for an injury, disease, condition, etc. that is set out in one medical ontology to an ontology that is used by the visualization system 100. For example, if the interface 110 receives patient data 112 requesting that an effect of a "heart attack" be rendered in the adjusted visualization 114, the interpreter 114 may determine that the adjustment relates to a "myocardial infarction." The interpreter 114 may then map the specification of the adjustment to be made to a "myocardial infarction" adjustment stored in the predefined adjustments 106 and/or to one or more data objects related to a heart. As another example, if the interface 110 receives patient data 112 identifying that a condition associated with a medical code, such as ICD-10 code "S72", is to be rendered in the adjusted visualization 114, the interpreter 114 may determine based on information regarding ICD-10 codes (or other medical codes) that the adjustment relates to a fracture of a femur. The interpreter 114 may therefore map the specification of the adjustment to be made to a "fractured femur" adjustment stored in the predefined adjustment 106 and/or to one or more data objects related to a femur.

The programmatic interface 110 may receive a specification as of adjustment at least partially in the form of an identification of a medical condition, injury, etc. as in the foregoing examples. Or, in some embodiments, the programmatic interface 110 may receive input of precise modification to be made to a visualization. For example, input may be received via the programmatic interface 110 that identifies a geometric modification, or a modification to an appearance, or other modification to be made to a manner of rendering an anatomical feature in a visualization 102 so as to produce an adjusted visualization 108.

The interface 116 may be additionally or alternatively be used in connection with receiving specifications of adjustments to be made to a visualization 102. For example, a GUI 118 may be used to output a visualization and to receive input with respect to adjustments to be made to the displayed visualization. For example, a user may select one or more anatomical features or one or more parts of an anatomical feature in the user interface and specify via the GUI 118 an adjustment to be made, such as by inputting via the GUI 118 (e.g., via selection from a list or other input) a disease or condition of that anatomical feature, annotating that anatomical feature, or otherwise adjusting a manner in which a visualization of the anatomical feature is rendered. When the user provides input indicating a selection of one or more anatomical features or the one or more parts of an anatomical feature, the visualization system, via the interpreter 114, may determine which features or parts are selected. For example, if user selects a location corresponding to a femur, the system may determine whether the user is indicating the leg, the upper leg, the femur, a portion of the femur, a point on the femur, or another object. The exact coordinate in the GUI 118 specified by the user input may be analyzed, alone or in connection with other user input (e.g., additional input by which the user disambiguates the initial selection), to determine an intended selection of the user. The intended selection may be one or more anatomical features or one or more portions of an anatomical feature. The visualization system, with the interpreter 114, may then determine the anatomical features and/or data objects to which the adjustment relates.

Accordingly, the visualization system 100, including through interpreter 114, may map a specification of an anatomical feature to which an adjustment relates to a data object related to that specification. Examples of techniques for such mapping are described in detail below.

The visualization system 100 is not limited to being implemented with a specific computing device or collection of computing devices, or limited to functionality being divided between any particular computing devices. For example, in some embodiments, all data and all adjustment and rendering may be performed on a server, and data for an adjusted visualization 108 may be transmitted to a client device for display. In other embodiments, all functionality of the system 100 may be implemented in one computing device.

Figure 1B:
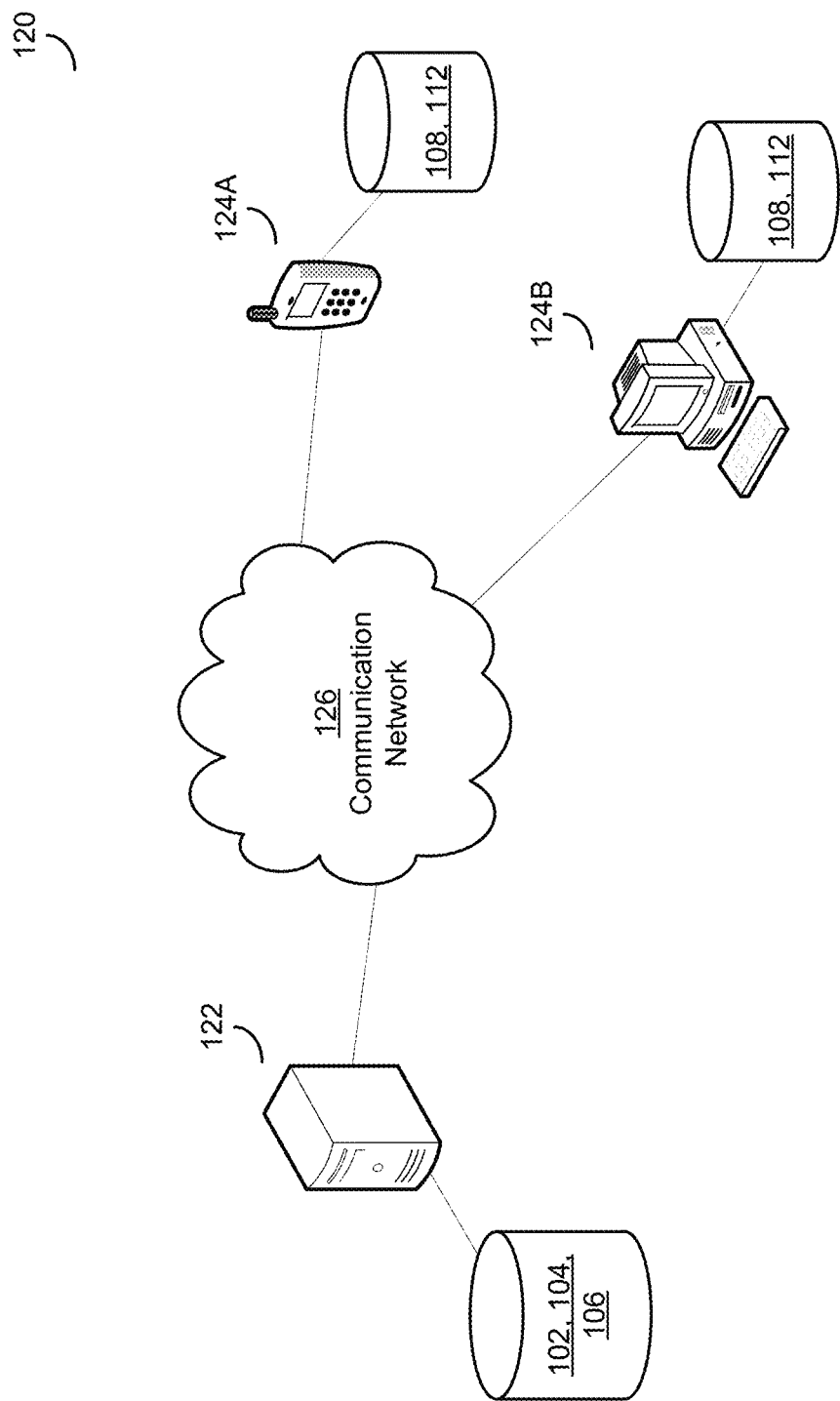
FIG. 1B is a diagram of some components of a computer system with which some embodiments may operate.

FIG. 1B illustrates an example of a computer system 120 with which some embodiments may operate. The system 120 includes a computing device 122 that may be implemented as a set of one, two, or more servers executing a server-side visualization facility. The computing device 122 may include a data store that stores data for visualizations 102, 104 and predefined adjustments 106, discussed above in connection with FIG. 1A. The system 120 may additionally include computing devices 124 (including device 124A and 124B, referred to individually and collectively herein as device(s) 124) that execute a client-side visualization facility. The devices 124 are illustrated in FIG. 1B as a mobile phone and as a desktop personal computer, but embodiments are not limited to operating with any particular form of computing device. The devices 122, 124 may communicate via a network 126, which may be any suitable one or more wired and/or wireless networks, including the Internet.

As shown in FIG. 1B, the device 124 may include a data store that stores patient data 112 and adjusted visualizations 108. In the example of FIG. 1B, the client-side visualization facility may include functionality for receiving input of specifications of adjustments to be made (e.g., via interfaces 110, 116 of FIG. 1A), mapping the specifications of adjustments to anatomical features and/or data objects, and producing adjusted visualizations. The client-side visualization facility may additionally store adjusted visualizations locally, in a data store of the device 124 or a data store accessible to the device 124. The inventors have recognized that implementing such functionality for processing, generating, and storing adjustments on a client device may be advantageous in some embodiments. For example, where adjustments relate to sensitive patient data, by implementing such functionality on a client device, the sensitive patient data is not transmitted to the device 122. The operator of the device 122, the operator of device 124, and the patient may therefore not be concerned regarding privacy of such patient data.

An example of a division of functionality between a server-side and a client-side visualization facility was given in connection with FIG. 1B. Those skilled in the art will appreciate from the discussion herein that embodiments are not limited to dividing functionality in any particular manner between devices. Below, for ease of description, reference may be made to a "visualization facility" executed by one or more computing devices. Such a facility may be executed by one device or functionality may be divided between facilities executing on multiple devices.

Figure 2:
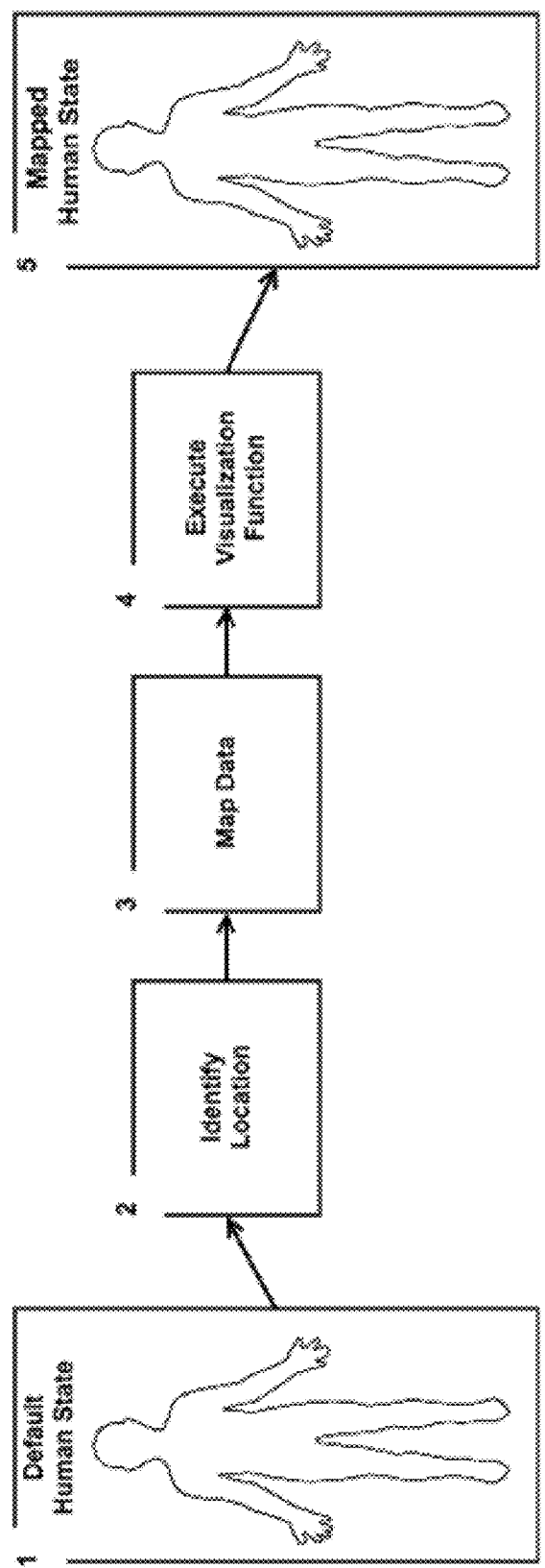
FIG. 2 is a flowchart of a process that may be implemented in some embodiments for processing received input regarding an adjustment to be made for generation of an adjusted visualization.

FIG. 2 illustrates an example of a workflow that may be performed by a visualization facility in accordance with embodiments described herein. The workflow of FIG. 2 includes five steps. Examples of ways in which these steps may be implemented are discussed in detail below, particularly in connection with FIGS. 6-8D.

At Step 1, as should be appreciated from the foregoing discussion of visualizations 102, 104, a visualization facility starts with a "default" human state that does not reflect an adjustment to be made. That default human state may be a "normal" or "healthy" state or may be another state such as a state associated with a condition or injury (e.g., obesity), as discussed above in connection with visualizations 102, 104. It is this default state of Step 1 that is to be edited with the specified adjustment.

At Step 2, a visualization facility receives a specification of an adjustment to be made, which includes a specification of a location at which the adjustment is to be made or displayed. The location may be specified in Step 2 in any of a variety of coordinate systems, ontologies, or other manners of specifying a location within a visualization of an anatomy. For example, the location may be specified as a two-dimensional or three-dimensional coordinate within a coordinate system of a displayed visualization, such as in the case that the adjustment is specified via a GUI. As another example, the location may be specified using a medical code, such as an ICD-10 code. As a further example, the location may be specified using an identifier for a disease, injury, procedure, or other medical terminology that is indicative of one or more affected anatomical features.

Figure 3:
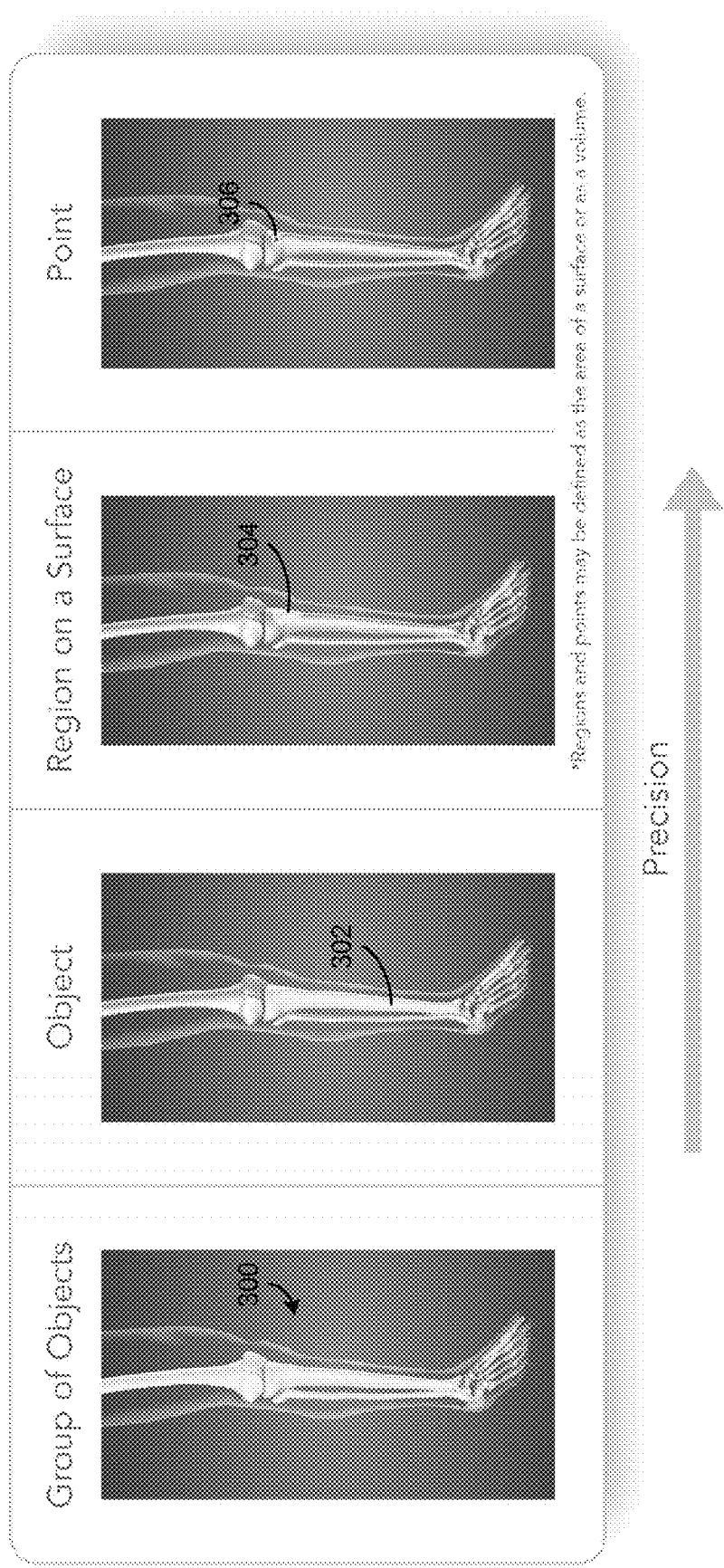
FIG. 3 provides examples of different levels of specificity that may be used for identifying a portion of a visualization to which a requested adjustment relates.

FIG. 3 illustrates various ways in which locations for adjustments may be specified, with increasing specificity. As should be appreciated from the foregoing, locations for adjustments may be specified as a group 300 of anatomical features (in the example of FIG. 3, the bones of a human right leg), an anatomical feature 302 (e.g., a human tibia), a portion 304 of an anatomical feature (e.g., a part of a surface of a human tibia), and a particular point 306 within an anatomical feature (e.g., a point on a surface of a human tibia).

In Step 3, the visualization facility maps that location specified for the adjustment in Step 2 to one or more anatomical features and/or one or more data objects related to those anatomical features. A discussion of mapping techniques that may be used in embodiments is provided below.

Following the mapping of the adjustment to data objects, in Step 4 a visualization function is executed. Through the visualization function, data for an adjusted visualization may be created. As discussed above, the adjusted visualization 108 that is output may include, in some embodiments, graphics data that, when provided to a graphics system of a computing device (e.g., a driver for a graphics card) can be output for display. The adjusted visualization 108 may additionally or alternatively, in some embodiments, include instructions for generating such graphics data, with the instructions set out using any suitable graphics instruction set, including according to a graphics library API (e.g., OpenGL, WebGL, etc.). The adjusted visualization 108 may additionally or alternatively, in some embodiments, include a hierarchy of data objects, similar to the hierarchy 102B described in detail above, that include information on how to render one or more anatomical features. The visualization function that is executed in Step 4 may be any suitable function to produce such visualization data, as embodiments are not limited in this respect.

In Step 5, the adjusted visualization presenting the human state with the adjustment mapped thereto is output. The output may be to a display, such as a display of a computing device. Additionally or alternatively, the output may be to a storage, such as a memory, and/or to a network for transmission to a recipient device where the visualization may be output to a display and/or to a storage.

As should be appreciated from the foregoing, the visualization facility may receive as input data of multiple different types for the creation of adjustments. This data, when received, may be processed by the visualization facility, such as through a workflow like the one illustrated in FIG. 2. Depending on a type of data that is received as input, different types of processing may be performed to produce an adjusted visualization.

Figure 4:
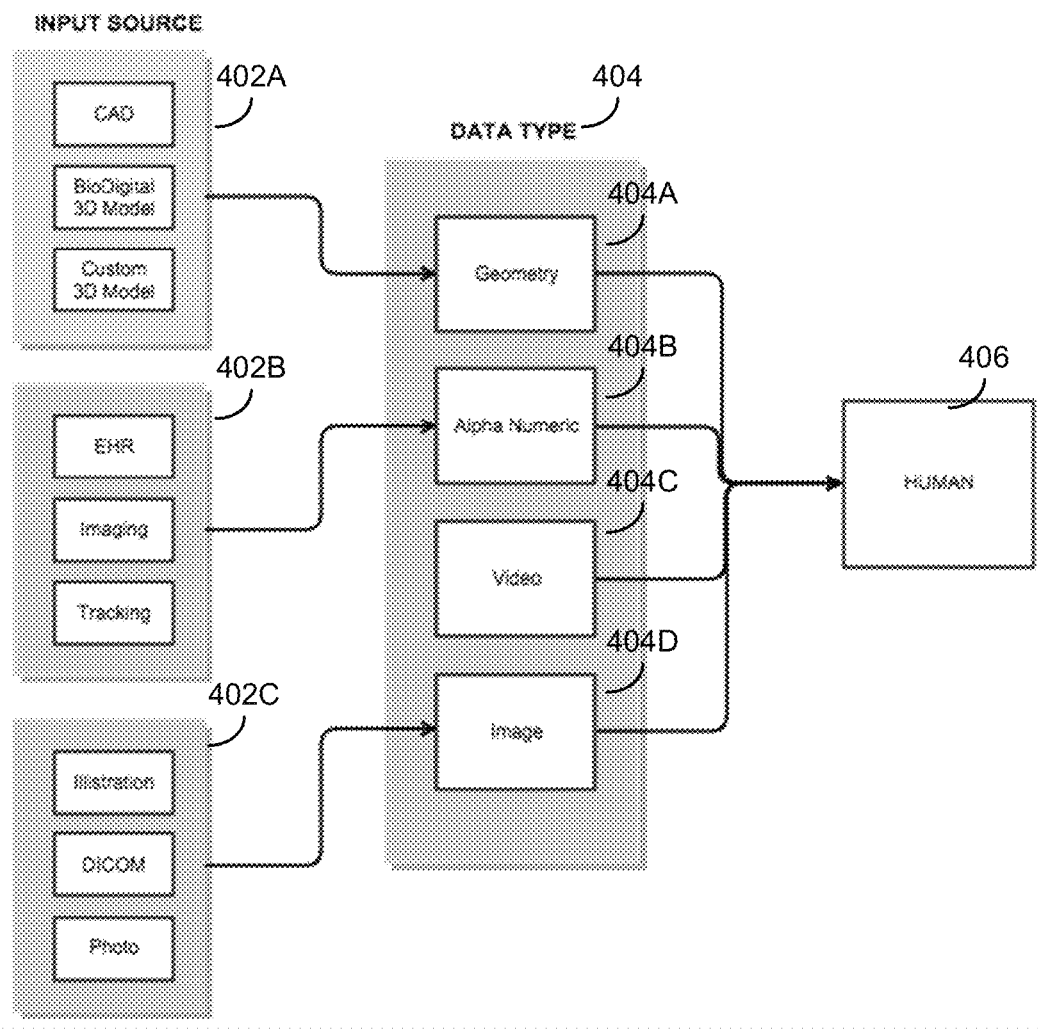
FIG. 4 identifies examples of types of input that may be included in a request to adjust a visualization.

FIG. 4 illustrates different types 404 of data that may be received in a specification of an adjustment to be made, and which may be processed as part of generating an adjusted visualization. The data types 404 illustrated in FIG. 4 include geometric inputs 404A, alphanumeric inputs 404B, video inputs 404C, and image inputs 404D. Each of these may be analyzed to generate an adjusted visualization 406 of anatomy.

Each of the data types 404 may be processed in a different manner to determine an adjustment specified by the data types, and a location at which the adjustment is to be made, including one or more anatomical features impacted by the adjustment.

For example, geometric inputs 404A may be (as shown through input sources 402A) computer-generated visualizations, including graphics or models for graphics. Such computer-generated visualizations may include Computer Assisted Design (CAD) models, a BioDigital 3D model of anatomy, or other custom 3D model. Such a visualization may visualize one or more anatomical features and indicate a manner in which one or more anatomical features are to be rendered in the visualization 406. For example, a geometric input 404A may be of an enlarged heart, thereby indicating that the visualization 406 is to be rendered with an enlarged heart. Processing the input 404A may include analyzing the content of a visualization and/or metadata for a visualization, to determine an anatomical feature to which the visualization corresponds. The processing may also include determining a type of adjustment requested through the visualization 404A, such as by analyzing the visualization 404A. For example, the analysis of the visualization may include comparing a geometry of the received visualization 404A to a base visualization, to determine variations. As another example, the analysis may include extracting from the visualization 404 information on a manner of rendering an anatomical feature and substituting the extracted information for corresponding information in a base visualization. In this manner, geometric information (e.g., values or equations defining geometry) may be extracted from a received visualization 404 and used to adjust a base visualization to create the visualization 406.

Alphanumeric inputs 404B may be content that includes words and/or numbers that may be structured and/or unstructured data. Such alphanumeric content 404B may include patient data such as doctors' dictations/notes, lab results, diagnoses, symptoms, or other information that may be included in an electronic health record, as shown in input sources 402B. In some cases, such patient data may not be exclusively alphanumeric data, but may additionally include imaging data described by the alphanumeric data. The alphanumeric data may also, in some embodiments, include tracking information derived from sensors worn by and/or implanted into a patient. Such alphanumeric content 404B may relate to one or more anatomical features, such as by indicating an injury, procedure (e.g., surgery), disease, genetic mutation, condition, or other factor that causes changes in anatomy. The alphanumeric input 404B may be processed to determine an anatomical feature to which a requested adjustment relates and a manner in which the adjustment is to be made. For example, alphanumeric input 404B may be analyzed to identify an injury, procedure, disease, etc. discussed in words or numbers, such as referred to explicitly in text using one or more medical terms or common-parlance synonyms for medical terms (e.g., "myocardial infarction" or "heart attack", or the ICD-10 code "S72"), or that are implied through numeric values or lab results included within the alphanumeric input 404B. The visualization facility may perform such an analysis using known semantic interpretation techniques and/or known pattern-matching or keyword-identification techniques. When such an injury, procedure, disease, etc. is identified by the visualization facility, it may be used to identify an anatomical feature impacted. For example, if the term "heart attack" appears, the visualization facility may determine that a heart attack is to be visualized.

The visualization facility may also determine a requested adjustment. For example, the alphanumeric input 404B may be text that is to be used to annotate a visualization, such as by labeling one or more anatomical features or otherwise associating text and/or an image with the anatomical feature(s). In such a case, once the anatomical feature to which the alphanumeric input 404B relates is identified by the visualization facility, the visualization facility may adjust the visualization 406 to include some or all of the alphanumeric input (and/or a related image) in the visualization 406. In a case that a geometric adjustment is requested, the visualization facility may attempt to determine a manner in which to make the geometric adjustment. In embodiments in which a visualization system includes predefined adjustments that define a manner in which an anatomical feature is to be rendered with a particular injury, procedure, disease, etc., the visualization facility may determine whether the predefined adjustments include information corresponding to the identified adjustment. If not, the visualization facility may additionally evaluate the alphanumeric input to determine whether geometry of an anatomical feature is specified.

Video input 404C may be audiovisual content relating to an injury, procedure (e.g., surgery), disease, genetic mutation, condition, or other factor that causes changes in anatomy. The visualization facility may analyze the video input 404C, including by analyzing the visual content and/or audio content to determine an anatomical feature to which the video input 404C relates. For example, by analyzing the video content in connection with information on known shapes or appearances of injuries, procedures, anatomical features, etc., the visualization facility may identify one or more anatomical features to which the video relates, and the video data may be analyzed to determine an adjustment requested by the video. As another example, audio for the video may include narrative speech that identifies anatomical features, or injuries, procedures, etc. to which a video relates, and the audio data may be analyzed with, for example, a speech recognizer to determine an adjustment requested by the video. Metadata may also be analyzed for information identifying an anatomical feature. The visualization facility may also determine a requested adjustment. For example, the video input 404C may be video that is to be used to annotate a visualization, such as by labeling one or more anatomical features with the video or otherwise associating the video with the anatomical feature(s). In such a case, once the anatomical feature to which the video input 404C relates is identified by the visualization facility, the visualization facility may adjust the visualization 406 to include some or all of the video input 404C in the visualization 406.

Similar to the analysis of a video 404C, in some embodiments an image 404D (which may be an illustration, DICOM medical image, photo, or other image 402C) may be received as input and analyzed to determine an anatomical feature to which it relates and/or an adjustment requested. The anatomical feature may be determined from content of the image 404D and/or metadata associated with the image 404D. The image input 404D may be an image that is to be used to annotate a visualization, such as by labeling one or more anatomical features with the image or otherwise associating the image with the anatomical feature(s). In such a case, once the anatomical feature to which the image input 404D relates is identified by the visualization facility, the visualization facility may adjust the visualization 406 to include some or all of the image input 404D in the visualization 406.

Figure 5A:
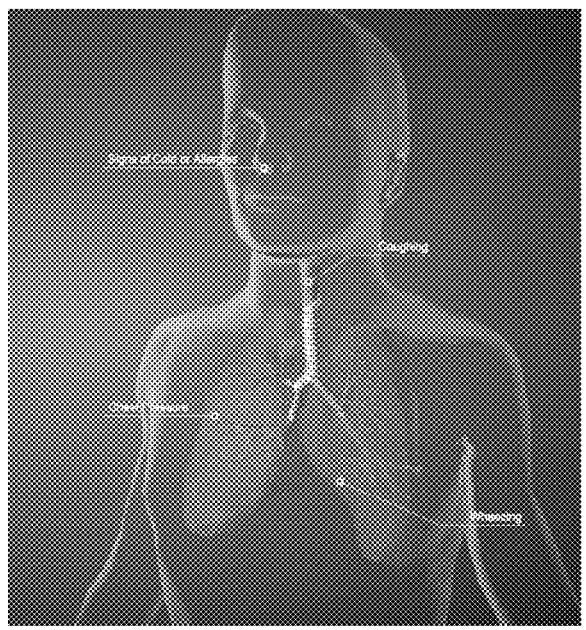
FIGS. 5A-5F depict examples of types of adjusted visualizations that may be produced in some embodiments.

Various types of adjustments may be made to visualizations through techniques described herein, as should be appreciated from the foregoing. FIGS. 5A-5F illustrate examples of types of adjustments that may be made. FIG. 5A, for example, illustrates a first type of adjustment, in which some anatomical components are made transparent while other anatomical components are colored, to highlight those anatomical components in the display. By increasing the transparency of some anatomical components, the remaining components may be displayed in context of surrounding anatomy while still being highlighted. FIG. 5A illustrates a second form of adjustment, with labels annotating anatomical features within the visualization. The adjustment for adding labels may include identifying locations at which annotations should be added, including anatomical features that are to be labeled by the annotations.

Figure 5B:
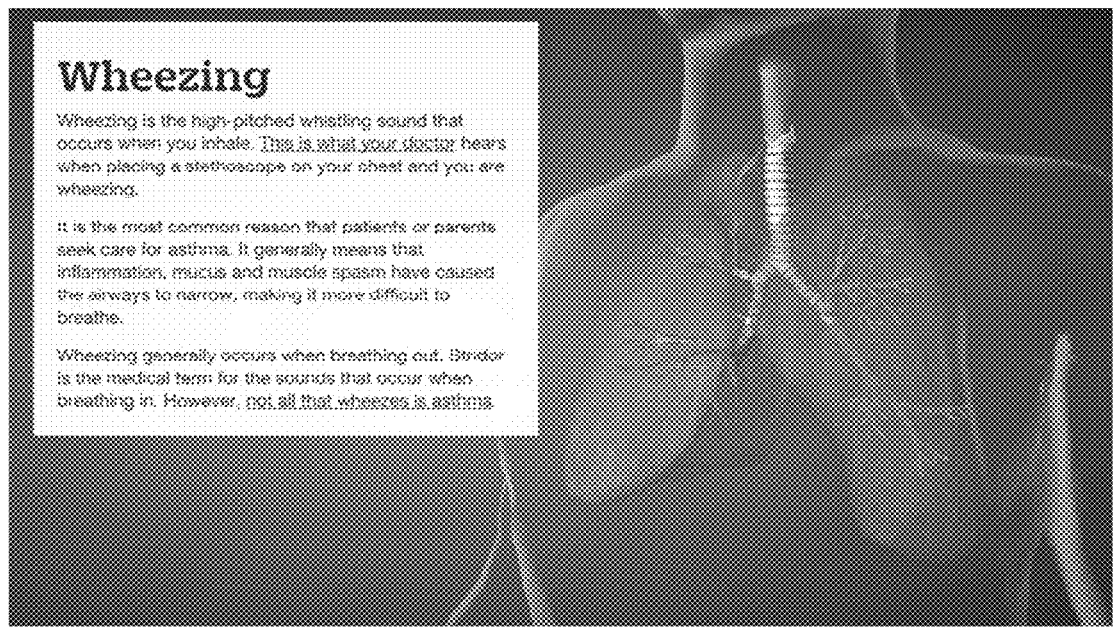

FIG. 5B illustrates a similar adjusted visualization, with additional text annotating the visualization. Here, the annotated text is related to lungs and defines a medical condition relating to lungs. When such text is received by the visualization system, as described above, an analysis of the text may determine that it relates to lungs and that the text should therefore be associated with the lungs in an adjusted visualization.

Figure 5C:
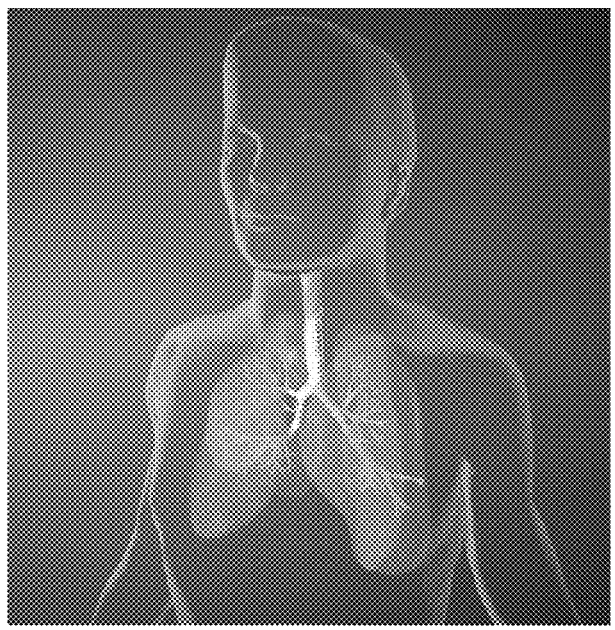
Figure 5D:
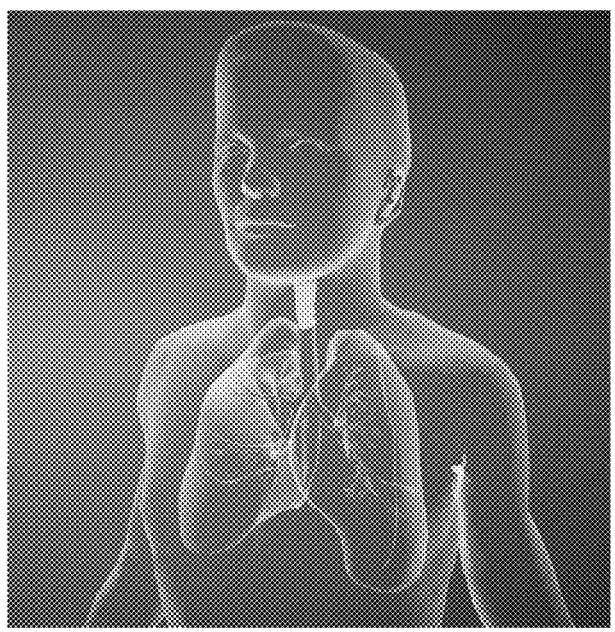

FIGS. 5C and 5D illustrate other manners in which to change an appearance of anatomical features in visualizations. In FIG. 5C, a color of respiratory features has been altered, while in FIG. 5D, a transparency of these anatomical features has been increased.

Figure 5E:
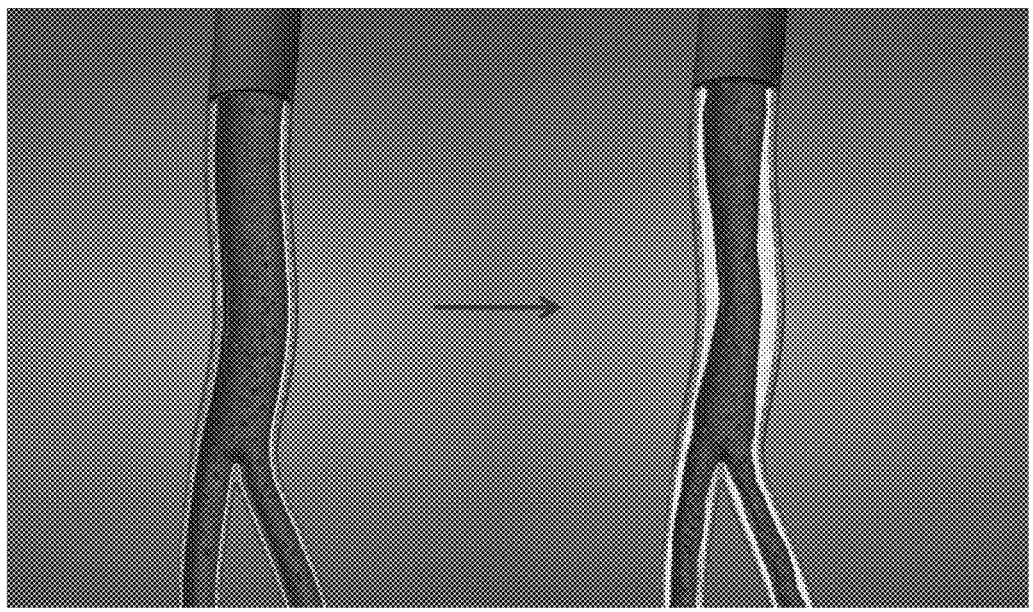

FIG. 5E illustrates a change in a rendering of an anatomical feature to show a medical condition, namely a blockage of vasculature. The left-hand view of FIG. 5E is a visualization of a "normal" blood vessel, while the right-hand view shows an adjusted visualization. The adjusted visualization includes additional material, which is the cause of the blockage of the vessel. That additional material may be, for example, cholesterol. Such an adjusted visualization may be produced in response to a request to render a visualization of vasculature for an "obese" patient, a request to render a visualization of vasculature having a blockage, a request to render a visualization with cholesterol deposits at a particular location, or other requested adjustment.

Figure 5F:
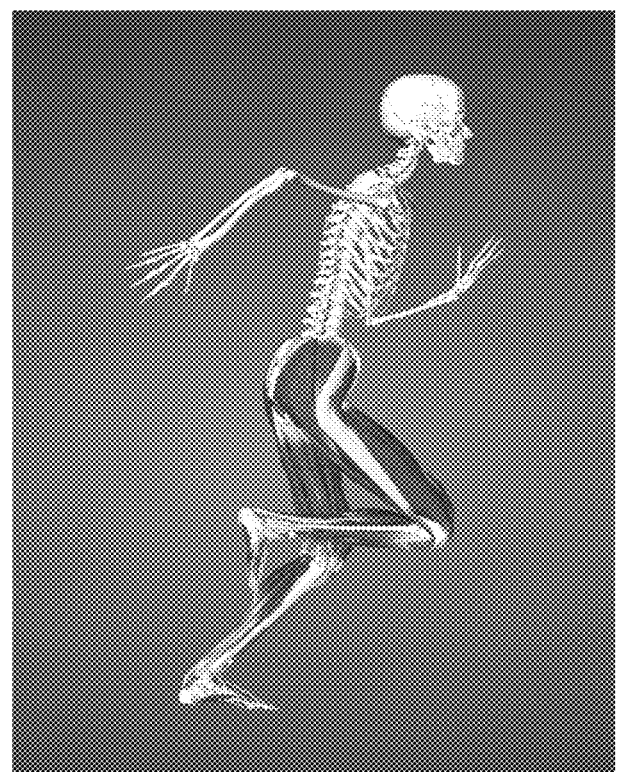

FIG. 5F illustrates another adjusted visualization that may be generated in some embodiments. The example of FIG. 5F illustrates one frame from an animated visualization, showing movements of a musculoskeletal system of a running human. During animation, multiple frames may be presented in sequence (e.g., as a video) to show how the anatomy moves. Such a visualization may be produced using stored information about movement of anatomy, or may be produced using motion capture data. For example, a patient may be monitored using movement detectors, such as a camera observing movement and/or sensors attached to the patient's body. Movements of the patient may be detected and, using known information about correspondences between particular larger movements (e.g., movements of a limb) and movements of anatomical features (e.g., particular muscles, tendons, bones, etc. within that limb), an animated real-time visualization of movements of the patient may be produced.

Note that in the visualization of FIG. 5F not all muscles are rendered, but rather an adjusted visualization is produced that includes the skeletal system and muscles of the lower torso and legs. This selective visualization of anatomy may be requested as an adjustment to either exclude certain anatomical features or include certain anatomical features.

Figure 6:
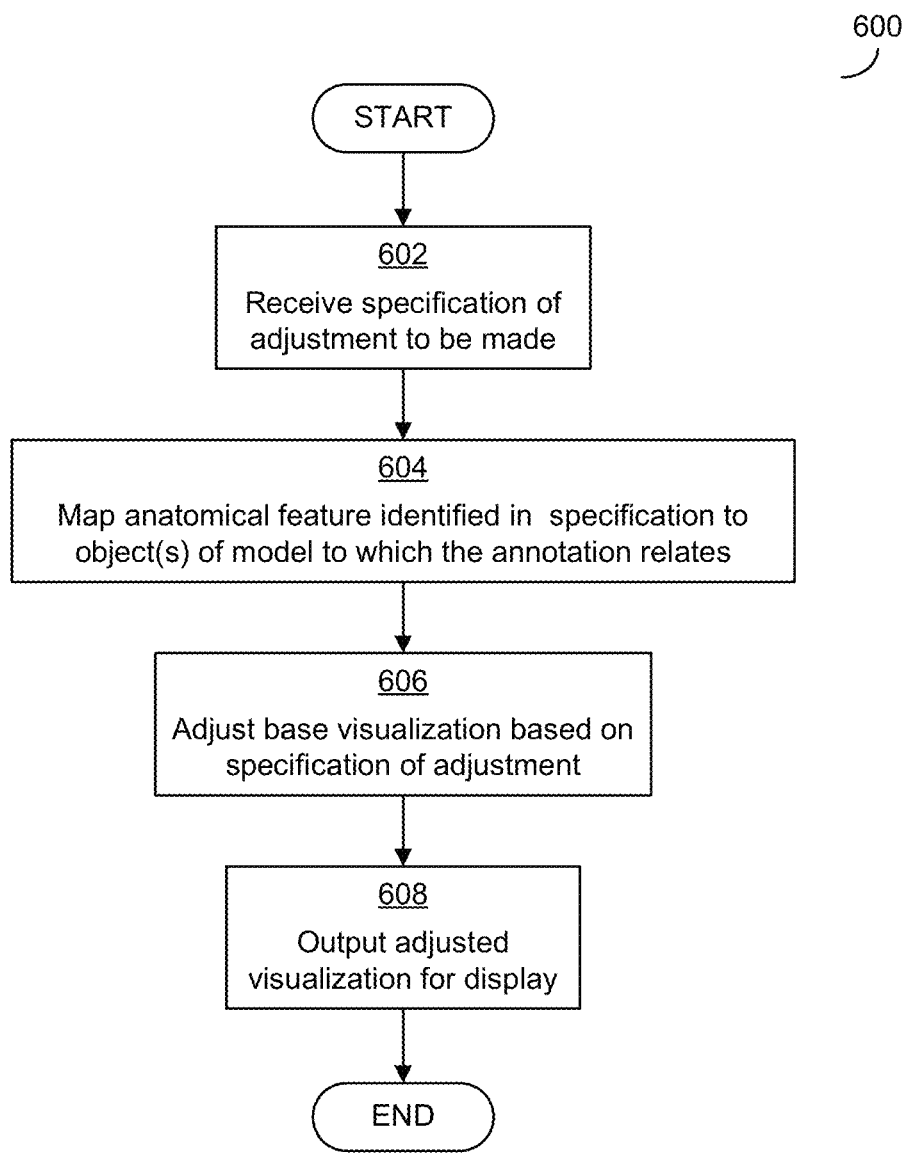
FIG. 6 is a flowchart of an illustrative process for adjusting a visualization of anatomy.

FIG. 6 illustrates an example of a process that may be performed by a visualization facility in some embodiments to produce an adjusted visualization based on an identification of an adjustment to be made. In some cases, prior to the start of the process 600, a base visualization may be presented, such as in a case that the adjustment is to be received via a graphical user interface. The base visualization that is used in the process 600 may be a visualization of "normal" or "healthy" anatomy, such as the visualization 102 described above in connection with FIG. 1A. Alternatively, the base visualization may have been edited in one or more ways as compared to the "normal" visualization, such as having been edited one or more times through a process like the process 600 to make one or more adjustments or by being a visualization defined for a different state of anatomy, such as a visualization for "obesity" or other condition, disease, injury, etc.

In block 602, the visualization facility receives a specification of an adjustment to be made to the base visualization to produce an adjusted visualization. The specification may be received in any suitable manner, including via a programmatic interface or a graphical interface. The specification may include an identification of an anatomical feature to which the adjustment relates as well as an identification of an adjustment to be made. The identification of the anatomical feature and the identification of the adjustment may be separate in some cases. For example, a user may select one or more anatomical features, or one or more parts of an anatomical feature, via a GUI and may additionally input information regarding an adjustment to be made. In another example, the visualization facility may receive via a programmatic input an identification of an anatomical feature and detailed information on an adjustment, such as geometric modifications to be made to a visualization of the identified anatomical feature. As another example, the visualization facility may receive via a GUI or programmatic interface an identification of an injury, medical condition, etc. that may indicate both an anatomical feature and an adjustment to be made to the visualization of that anatomical feature. The ICD-10 code "S72" and "heart attack" examples above are examples where the input may identify both the anatomical feature and the adjustment to be made.

In block 604, the visualization facility maps the anatomical feature specified in the adjustment to one or more data objects of the hierarchy of the base visualization to be adjusted. The visualization facility may map the adjustment based on a manner in which the adjustment is specified in block 602. For example, where the specification received in block 602 explicitly identifies an anatomical feature, the visualization facility in block 604 may determine the data objects of the hierarchy that define that anatomical feature in the base visualization, that define a region of the base visualization to which the adjustment relates, and/or that store the data (e.g., geometry information, or other information) regarding the anatomical feature that is to be edited. For example, if the adjustment relates to annotating a heart, the mapping in block 604 may determine one or more data objects that relate to a heart. As another example, if the adjustment relates to visualizing a heart murmur in one valve of a heart, the visualization facility in block 604 may determine, from among one or more data objects defining a heart, which data objects define geometric information for that valve of the heart.

As discussed in detail below, the mapping of block 604 may be performed in a variety of ways dependent on the nature of the specification received in block 602. Accordingly, in some embodiments, the mapping of block 604 may include determining a manner in which the specification is provided. For example, the specification may be analyzed to determine whether it was provided via a programmatic interface or via a graphical interface. The input specification may also be analyzed to determine whether it is one of the input types identified in connection with FIG. 4. When the manner in which the input is received and the format of the input are determined, the visualization facility may select a manner in which to process the specification to determine the anatomical feature to which it relates and then determine the data objects. For example, the visualization facility may determine whether a text analysis (e.g., keyword mapping) or audio analysis (e.g., speech recognition) is to be performed, as discussed above.

In block 606, once the data objects are identified through the mapping of block 604, the visualization facility adjusts the base visualization based on the specification of the adjustment to be made. As should be appreciated from the foregoing, including the discussion of FIGS. 5A-5F, various types of adjustments may be made. These may include annotating anatomical features, omitting or including anatomical features from a visualization, changing a manner in which an anatomical feature is rendered, or other adjustments. Based on the adjustment requested in the specification received in block 602, one or more changes are made in block 606. For example, in block 606, the base visualization may be adjusted to add a text annotation (either a label or longer narrative text) that is related to an anatomical feature included in the visualization, as in FIGS. 5A and 5B. As another example, in block 606, the base visualization may be adjusted to modify a geometry of one or more anatomical components defined by one or more data objects, and in such a case information on a geometry that is stored in one or more data objects may be edited to contain a new value and/or new equation, or other new information defining the new geometry.

To make the modifications, new copies of the data objects of a hierarchy for a base visualization (e.g., a new copy of hierarchy 102B of visualization 102 of FIG. 1A) may be produced in some embodiments. In other embodiments, as information is read from data objects and then used in rendering a visualization based on the data objects, the information contained within the data objects may be edited before rendering, such that the edited information is used in the rendering.

The adjusted visualization that is produced in block 606 may be in any suitable format, as embodiments are not limited in this respect. For example, the adjusted visualization may include, in some embodiments, graphics data that, when provided to a graphics system of a computing device (e.g., a driver for a graphics card) can be output for display. The adjusted visualization may additionally or alternatively, in some embodiments, include instructions for generating such graphics data, with the instructions set out using any suitable graphics instruction set, including according to a graphics library API (e.g., OpenGL, WebGL, etc.). The adjusted visualization may additionally or alternatively, in some embodiments, include a hierarchy of data objects, similar to the hierarchy 102B described in detail above in connection with FIG. 1A, that include information on how to render one or more anatomical features.

In block 608, once the visualization facility produces the adjusted visualization in block 606, the adjusted visualization may be output for display. In a case that the visualization facility executes on a same computing device as the adjusted visualization is to be displayed, the facility may output the adjusted visualization to one or more components of the computing device (e.g., rendering engine, graphics processing unit, graphics driver, graphics card, etc.) to display the adjusted visualization on a screen. In other embodiments, the visualization facility may execute on a different computing device and the facility may output the adjusted visualization to a storage (e.g., memory) or a network adapter for transmission over one or more networks.

Once the adjusted visualization is output in block 608, the process 600 ends. Following the process 600, an adjusted visualization is available for presentation to a user to enable the user to better view and understand anatomy with the requested adjustment.

Figure 7A:
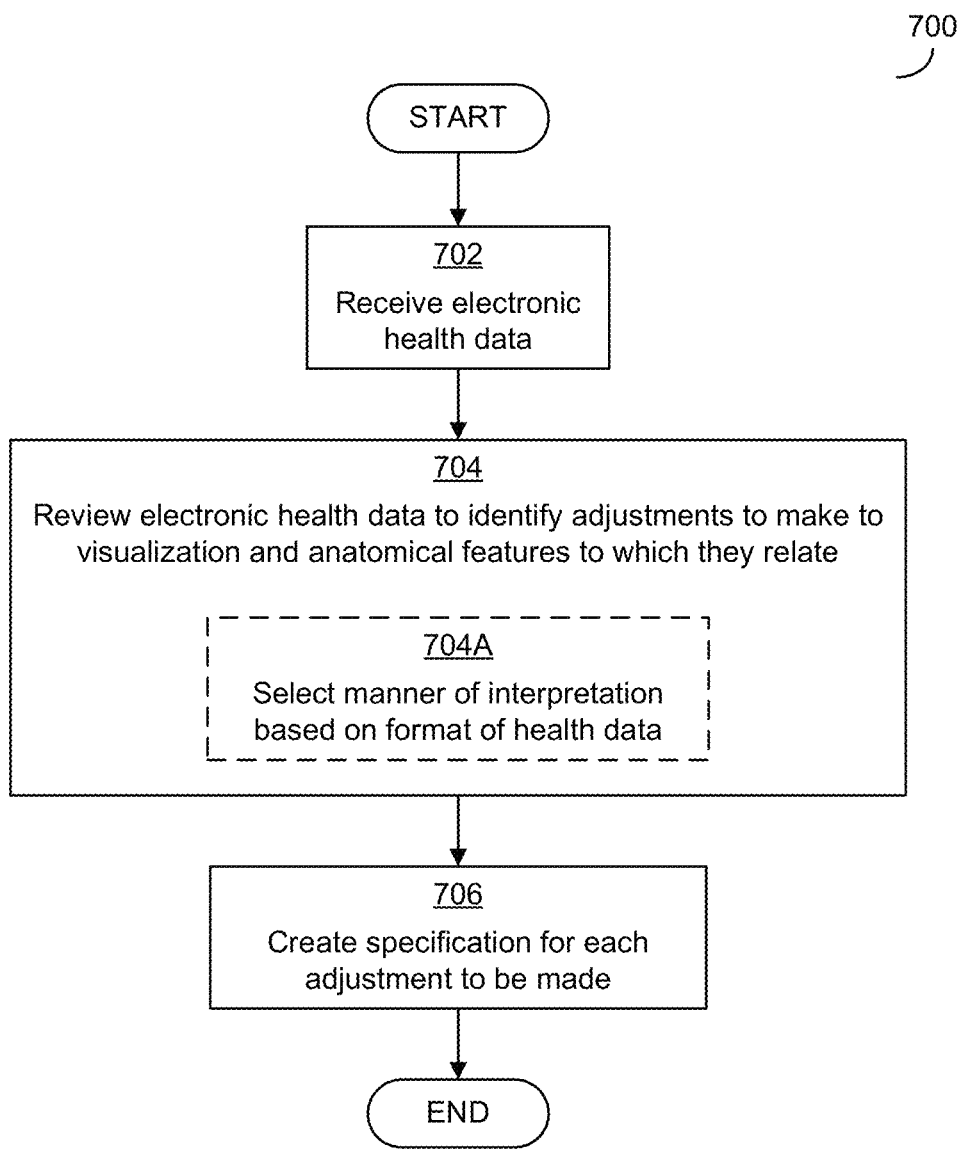
FIGS. 7A-7B are flowcharts of processes that may be implemented in some embodiments for receiving specifications of adjustments to be made to visualizations.
Figure 7B:
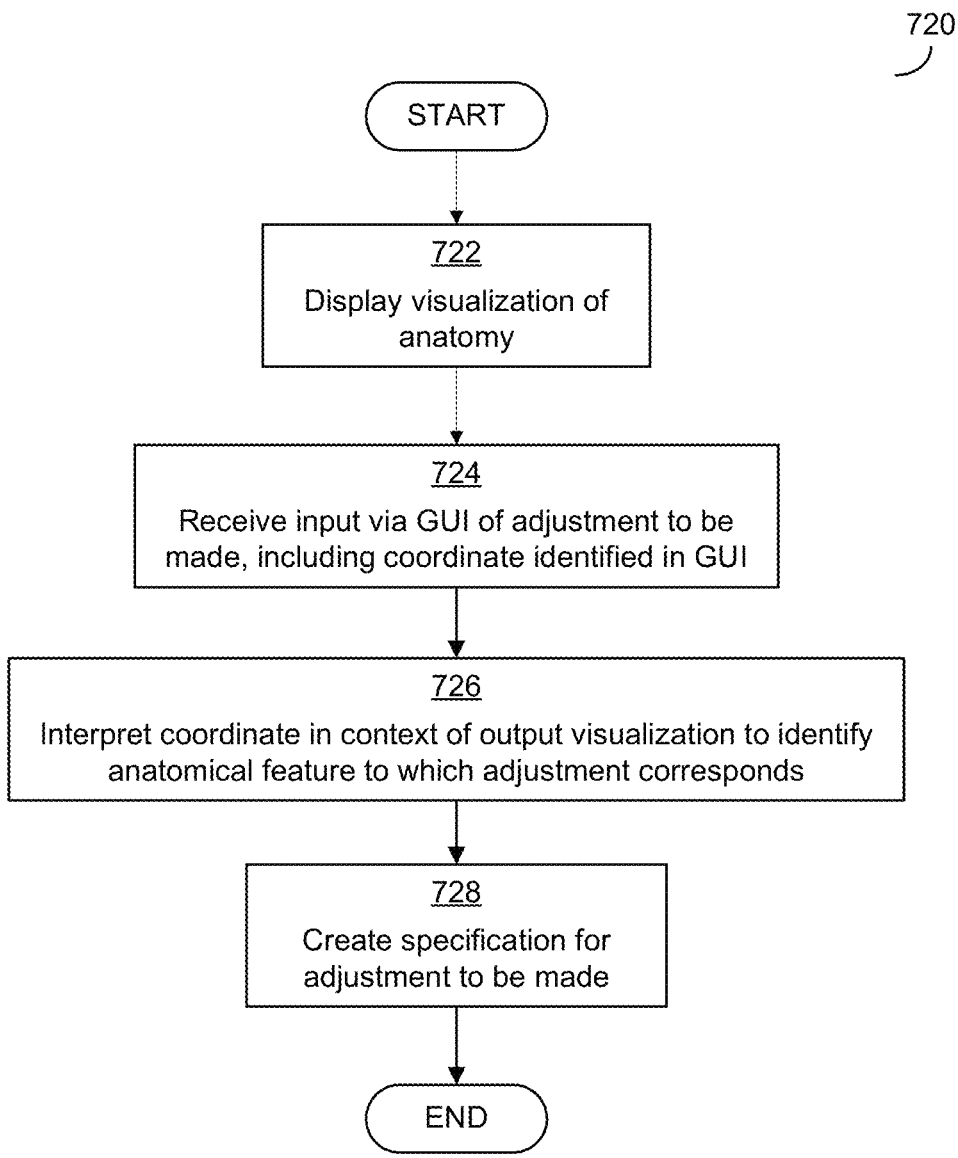

FIGS. 7A and 7B illustrate examples of processes that may be performed by a visualization facility for generation of specifications for adjustments based on received information. The process 700, 720 of FIGS. 7A-7B may be performed, for example, by an interpreter such as the interpreter 114 discussed above in connection with FIG. 1A. The processes may be used to translate received information that is indicative of a requested adjustment into an adjustment that may be made to a visualization to produce an adjusted visualization.

The process 700 of FIG. 7A begins in block 702, in which a visualization facility receives, such as via a programmatic interface, electronic health data. The electronic health data may be for a patient and may be formatted in any suitable manner, including according to known data structures and formats for an Electronic Health Record (EHR). In block 704, the visualization facility reviews the electronic health data to identify adjustments to be made and anatomical features to which the adjustments relate. This may include parsing the electronic health data to identify each injury, procedure (e.g., surgery), disease, genetic mutation, condition, or other piece of medical information included within the electronic health data that may affect anatomy and that may be visualized.

It should be appreciated from the foregoing that electronic health data may include information formatted and stored in a variety of different ways. The electronic health data may include, for example, structured and/or unstructured text, images, audio (e.g., doctor's dictations), video, and/or other data. Moreover, as should be appreciated from the foregoing discussion of at least FIG. 4, within each form of data the review may be different. For example, for structured and/or unstructured text, the review may determine whether health information is set out using explicit medical terminology (e.g., "myocardial infarction"), common parlance for medical conditions (e.g., "heart attack"), or medical codes (e.g., ICD-10 code S72 for a fractured femur). The review of the electronic health data in block 704 may therefore be dependent on a form of the electronic health data, and may include making a determination of the form of the electronic health data so as to determine a manner in which to review the electronic health data.

Accordingly, in block 704A the visualization facility determines a form of each unit of electronic health data and, for each unit of electronic health data, selects a manner of interpretation for that unit.

The review of block 704, using the manner of interpretation selected in block 704A, may allow for identification of medical conditions, etc. that relate to anatomical features and that are to be visualized. Accordingly, based on the review of block 704, the visualization facility creates in block 706 a specification for each adjustment to be made. The specification created in block 706 may include an identification of an anatomical feature to which an adjustment relates and a specification of the requested adjustment.

The specification of the requested adjustment may vary, dependent on an amount of detail set out in the electronic health data. For example, if the visualization facility determines that the electronic health data merely identifies "fractured femur" using ICD-10 code S72 without identifying a location of the fracture within the femur or more information regarding the fracture, the visualization facility may use a default manner of identifying an adjustment for a fracture, such as by specifying that the bone is to be rendered with a fracture located in a middle of the bone or by requesting an annotation of the bone that identifies a fracture without rendering the fracture. In contrast, if the visualization facility determines through the review that the electronic health data indicates that a skin growth of a particular type (e.g., "mole") is located "5 cm" above the patient's right knee, the visualization facility may produce a specification for an adjustment indicating that a mole is to be rendered on the visualized skin at a location corresponding to 5 cm above the right knee.

Once a specification is created for each adjustment to be made, the process 700 ends.

FIG. 7B illustrates a flowchart for a process 720 that may be implemented by a visualization facility to create a specification of an adjustment to be made based on an input received via a graphical user interface. As with the process 700 of FIG. 7A, the process 720 of FIG. 7B may be implemented by an element such as the interpreter 114 of FIG. 1A.

The process 720 begins in block 722, in which a visualization of anatomy is displayed. The visualization that is output in block 722 may be a "normal" or "healthy" visualization, such as the visualization 102 described above in connection with FIG. 1A. Alternatively, the visualization may have been edited in one or more ways as compared to the "normal" visualization, such as having been edited one or more times through a process like the process 600 to make one or more adjustments or by being a visualization defined for a different state of anatomy, such as a visualization for "obesity" or other condition, disease, injury, etc. This visualization that is displayed in block 722 may be a "base" visualization that is to be adjusted with one or more adjustments.

In block 724, the visualization facility receives via a graphical user interface an input of an adjustment to be made, including a coordinate selected in the GUI. The coordinate selected in the GUI may be a precise two- or three-dimensional coordinate within the GUI. The input of the adjustment to be made may identify an injury, procedure (e.g., surgery), disease, genetic mutation, condition, or other factor that causes changes in anatomy and may identify a manner in which the adjustment is to be made, such as through an annotation, a geometric modification, etc. The input on the adjustment to be made may be provided through the GUI in any suitable manner, including by selecting options from a menu or otherwise providing input using suitable user interface techniques.

By selecting the coordinate in block 724, a user may be indicating one or more anatomical features or portions of anatomical features, such as any of the specifications discussed above in connection with FIG. 3. Accordingly, in block 726, the visualization facility interprets the selected coordinate in context of the output visualization and/or other information provided by the user via the GUI to determine the anatomical feature to which the adjustment is to correspond. This may include, for example, determining an anatomical feature that was displayed in the visualization in the GUI at the coordinate, such that the selected coordinate is within the anatomical feature. This may additionally include, for example, determining whether the user provided another input indicating that the selection is of a portion of an anatomy. For example, the user may provide input via a GUI (e.g., by pushing a button, holding a key on a keyboard, or providing another input) that the selection is of only a portion of an anatomical feature, or of a particular point within the anatomical feature. Similarly, the user may provide an input via the GUI that the user is indicating a collection of anatomical features, such as an entirety of a limb or a collection of bones. As another example, in some embodiments the GUI may allow a user to hover a pointer over different portions of a display of an anatomical feature and, at specific locations, select the entirety of the anatomical feature or different regions of an anatomical feature, or at other locations select points within the anatomical feature. In such an embodiment, by determining the location at which the pointer was hovering when the selection was made, a determination of which anatomical feature, region of an anatomical feature, or point was selected by the user.

In block 728, based on the specified adjustment provided in block 724 and the anatomical feature determined in block 724, the visualization facility creates a specification of an adjustment to be made. Once the specification is made, the process 720 ends.

Various examples were described above of ways in which adjusted visualizations may be produced, for different types of adjustments. FIGS. 8A-8D illustrate flowcharts for creating adjusted visualizations for specific examples of adjustments. It should be appreciated, however, that the examples of FIGS. 8A-8D are merely illustrative and that other processes or other adjustments may be used.

Figure 8A:
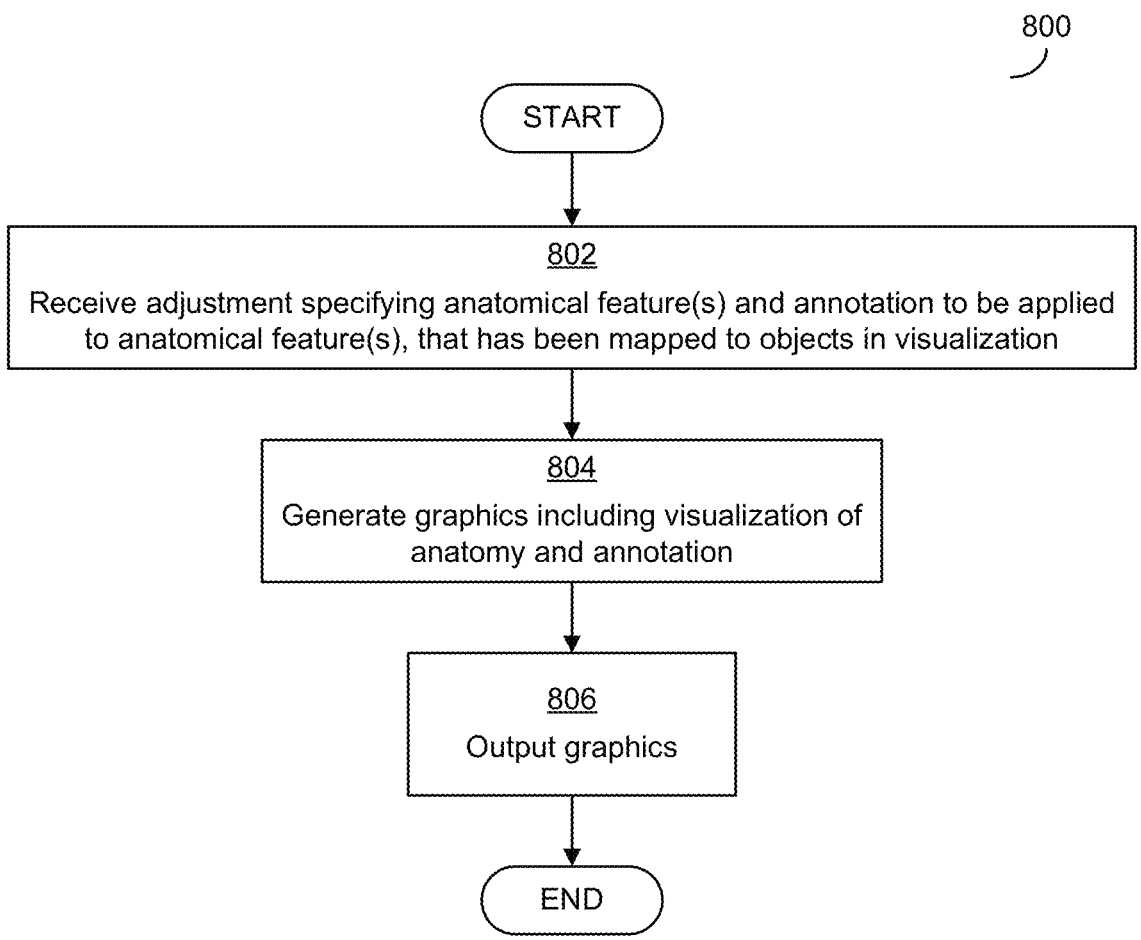
FIGS. 8A-8D are flowcharts of illustrative processes for generating adjusted visualizations based on specifications of adjustments to be made.

The process 800 of FIG. 8A may be used to generate an adjusted visualization that includes an annotation for a particular anatomical feature, such as the labels or narrative text shown in the examples of FIGS. 5A and 5B. The process 800 begins in block 802, in which the visualization facility receives input of an adjustment that specifies one or more anatomical features and that specifies an annotation to be applied to the feature(s). The annotation may include any suitable content, including text, images, video, audio, and/or other content. The adjustment may have already been mapped to one or more data objects of a base visualization to be annotated, such as using mapping techniques described above.

In block 804, the visualization facility generates computer graphics including the visualization of the anatomy as well as the annotation. The visualization facility may generate the graphics in any suitable manner, including by rendering graphics data based on instructions for rendering, such as instructions set out in a graphics library API (e.g., OpenGL, WebGL, or others). The visualization facility may generate the graphics for the visualization of the anatomy based on data available in data objects for a base visualization, such as by rendering based on instructions set out in the data objects and/or by generating instructions from other information stored in the data objects indicative of a manner in which to represent anatomical features and then rendering those instructions. Based on the specification of the annotation in the adjustment, the visualization facility may generate appropriate graphics instructions for generating graphics data such that the annotation is displayed in the visualization alongside graphics data for the anatomical features. For example, the visualization facility may generate instructions that, when processed by a graphics engine, create graphics data that display the text or images of the annotation. The visualization facility may additionally or alternatively generate instructions that create graphics data enabling playback of video and/or audio. The visualization facility may generate the instructions such that, when processed to generate graphics data, the instructions also indicate a link to one or more anatomical features of the visualization. For example, when the visualization facility generates instructions to display text for a label, the visualization facility may also generate instructions for a line or other indicator to be produced identifying a link between the text of the label and the anatomical feature that is being labeled. Once such graphics instructions are generated by the visualization facility, the instructions may be processed by a graphics engine alongside other graphics instructions for one or more anatomical features to generate a graphical visualization of both the anatomical features and the annotation.

Once the graphics are generated in block 804, the visualization facility outputs the graphics in block 806. The output may be to a display, to a memory, or to a network, as should be appreciated from the foregoing discussion of FIG. 6.

Figure 8B:
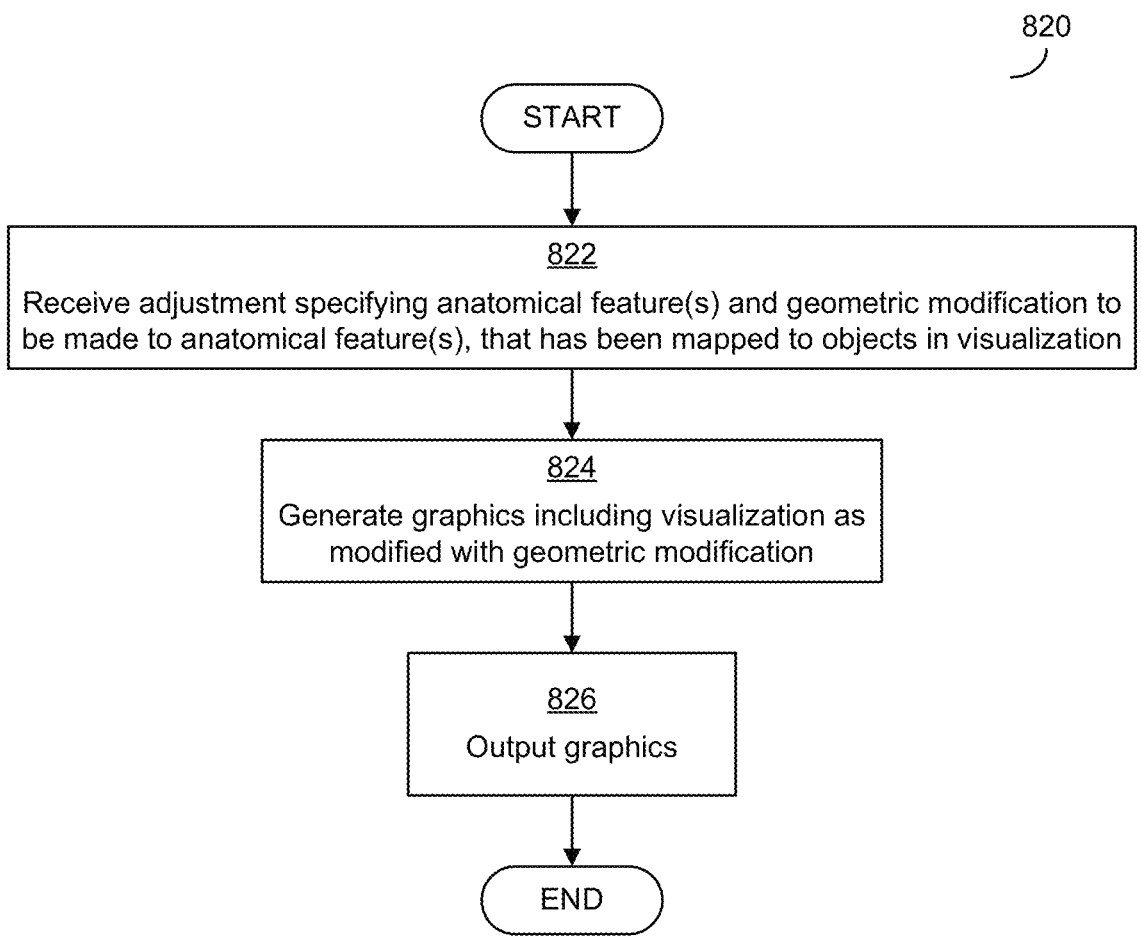

FIG. 8B illustrates another example of an adjustment, which relates to a specific geometric modification that may be made to a base visualization of an anatomical feature. Such a geometric modification may be made to display an anatomical feature with a different dimensions and/or shape, such as to visualize a heart of an athlete (as compared to a non-athlete), to visualize a bronchial tubes of a person with asthma, or other anatomical feature.

The process 820 begins in block 822, in which a visualization facility receives an adjustment specifying one or more anatomical features that are to be modified and indicating a geometric modification to be made to the anatomical feature(s). The adjustment may have already been mapped to one or more data objects of a base visualization to be annotated, such as using mapping techniques described above.

The geometric modification may be specified in the input received in block 822 in any suitable manner. In some embodiments, for example, a factor by which to increase a size of one or more dimensions of an anatomic feature may be set, which may be a constant amount, a scaling factor, or other factor. The factor may be a value or an equation, or specified in any other suitable manner. As another example, in some embodiments an equation or set of values defining a new dimension or shape for an anatomical feature may be received.

In block 824, the visualization facility generates graphics including the visualization as modified with the geometric modification identified by the input received in block 822. As discussed above in connection with FIG. 8A, the visualization facility may generate the graphics in block 824 by rendering graphics instructions using a graphics library, including by rendering graphics instructions set out in a graphics library API like OpenGL or WebGL. In such a case, graphics instructions may be stored by data objects of a base visualization that relate to the anatomical feature(s) identified in block 822, and/or may be generated by the visualization facility from information stored by the data objects. The visualization may modify such graphics instructions based on the geometric modification that is to be made, either by editing the graphics instructions stored by the data objects or by editing the information stored by the data objects so as to generate different graphics instructions. The manner in which the geometric modification is made may depend on a manner in which the modification is specified in block 822. For example, if the geometric modification is identified by a factor (e.g., expand every dimension by 1 cm, or render with 2× size), that factor may be used to modify the existing geometric information of the graphics instructions or data objects. As another example, if the geometric modification indicates a substitute dimension or shape, that substitute dimension or shape may be used to replace the existing geometric information of the graphics instructions or data objects.

Once the graphics are generated in block 824, the visualization facility outputs the graphics in block 826. The output may be to a display, to a memory, or to a network, as should be appreciated from the foregoing discussion of FIG. 6. The process 820 then ends.

Figure 8C:
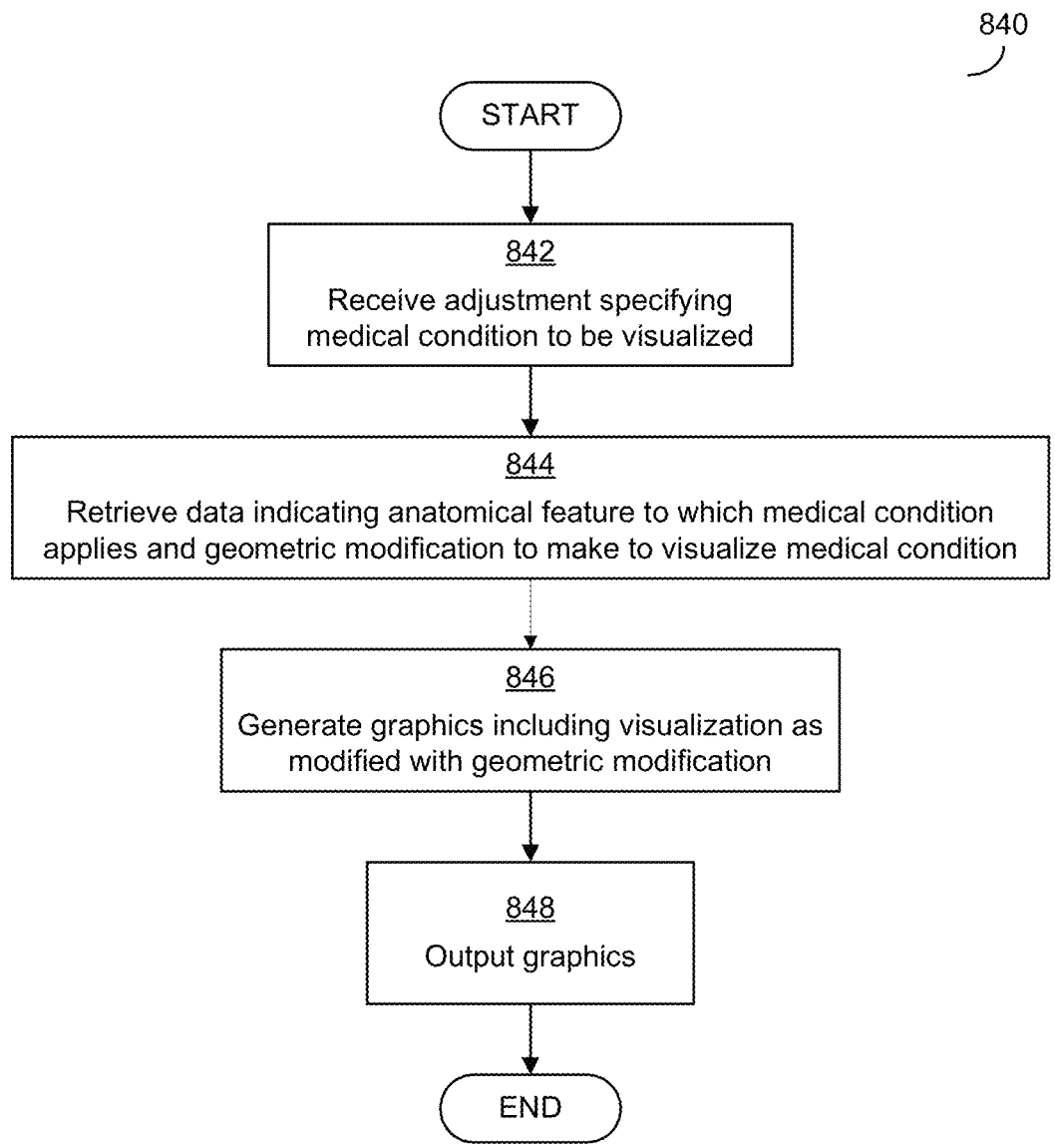

FIG. 8C illustrates another example process 840 for visualizing an effect of a particular medical condition (or injury, result of an operation, etc.) on anatomy. The process 840 begins in block 842, in which a visualization facility receives a specification of an adjustment to be made, which identifies a particular medical condition. In block 844, based on the identification of the medical condition, the visualization facility retrieves from a data store an indication of an anatomical feature to which that medical condition relates and an identification of a geometric modification to be made to visualize that medical condition. The data store may include information on multiple different medical conditions (and injuries, results of operations, etc.) and geometric modifications that may be made to visualize each, such as the data store 106 discussed above in connection with FIG. 1A.

Once the geometric modification for visualizing the medical condition has been retrieved, the geometric modification may be used in generation and output of graphics in blocks

846, 848. The operations of blocks 846, 848 may be similar to those discussed above in connection with blocks 824, 826, of FIG. 8B and therefore, for the sake of brevity, will not be discussed further herein. Once the graphics are output in block 848, the process 840 ends.

While not illustrated in FIG. 8C, it should be appreciated that, in some embodiments and for some inputs, the visualization facility may determine that there is no pre-stored information for visualizing of the particular medical condition specified. In response to such a determination, the visualization facility may output a message for presentation to a user identifying that the visualization facility does not have sufficient information to effect the requested visualization and requesting additional information. The user may be given the option, for example, to input specific parameters for a geometric modification. In such a case, the visualization facility may proceed with a process like the one discussed above in connection with FIG. 8B.

Figure 8D:
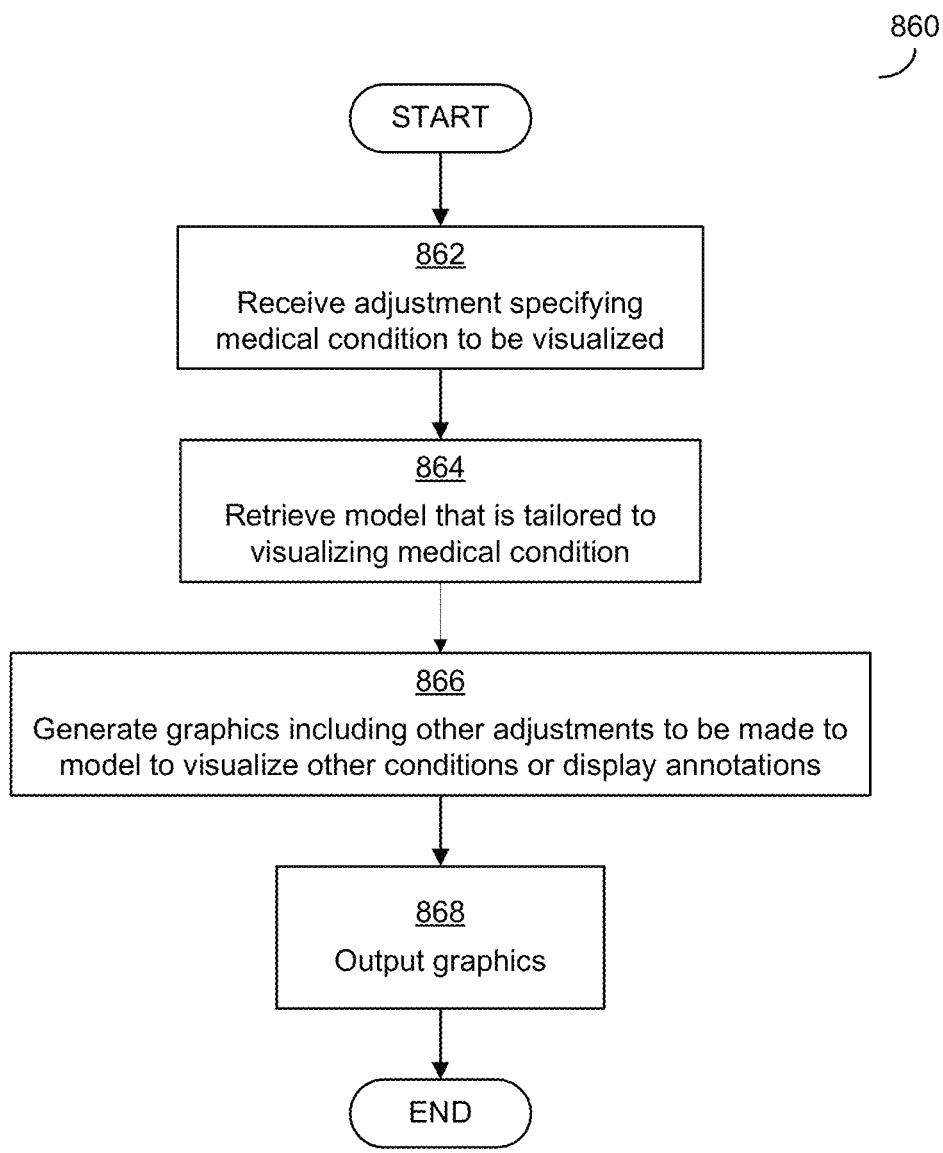

FIG. 8D illustrates a flowchart for a process 860 that may be used in some embodiments for visualizing an effect of a particular medical condition (or injury, result of an operation, etc.) on anatomy. In contrast to the process 840 of FIG. 8C, which included making modifications to a base visualization to effect the visualization, the process 860 of FIG. 8D may include changing the base visualization. As discussed above in connection with visualizations 104 of FIG. 1A, in some embodiments a visualization facility may be configured with one or more base visualizations that already account for one or more variations from a "normal" or "healthy" anatomy to visualize a different state of the anatomy, such as a different state resulting from an injury, disease, medical condition, or other factor that may impact anatomy.

The process 860 begins in block 862, in which the visualization facility receives input specifying an adjustment, which relates to a medical condition to be visualized. In response to receipt of the input identifying the medical condition, the visualization facility determines that there is a corresponding visualization for the medical condition, and in block 864 retrieves that visualization and corresponding data objects. The visualization facility may then in block 866 render graphics based on that visualization, including using techniques described above for generation or processing of graphics instructions. In addition, in block 866, the visualization facility may make one or more further adjustments to the retrieved visualization, such as using any of the techniques described herein. The generation of the graphics in block 866, and the output of the graphics in block 868, may be similar to those discussed above in connection with blocks 824, 826, of FIG. 8B and therefore, for the sake of brevity, will not be discussed further herein. Once the graphics are output in block 868, the process 860 ends.

While not illustrated in FIG. 8D, as with FIG. 8C, it should be appreciated that, in some embodiments and for some inputs, the visualization facility may determine that there is no pre-stored information for visualizing of the particular medical condition specified. In response to such a determination, the visualization facility may output a message for presentation to a user identifying that the visualization facility does not have sufficient information to effect the requested visualization and requesting additional information. The user may be given the option, for example, to input specific parameters for a geometric modification. In such a case, the visualization facility may proceed with a process like the one discussed above in connection with FIG. 8B.

Figure 9:
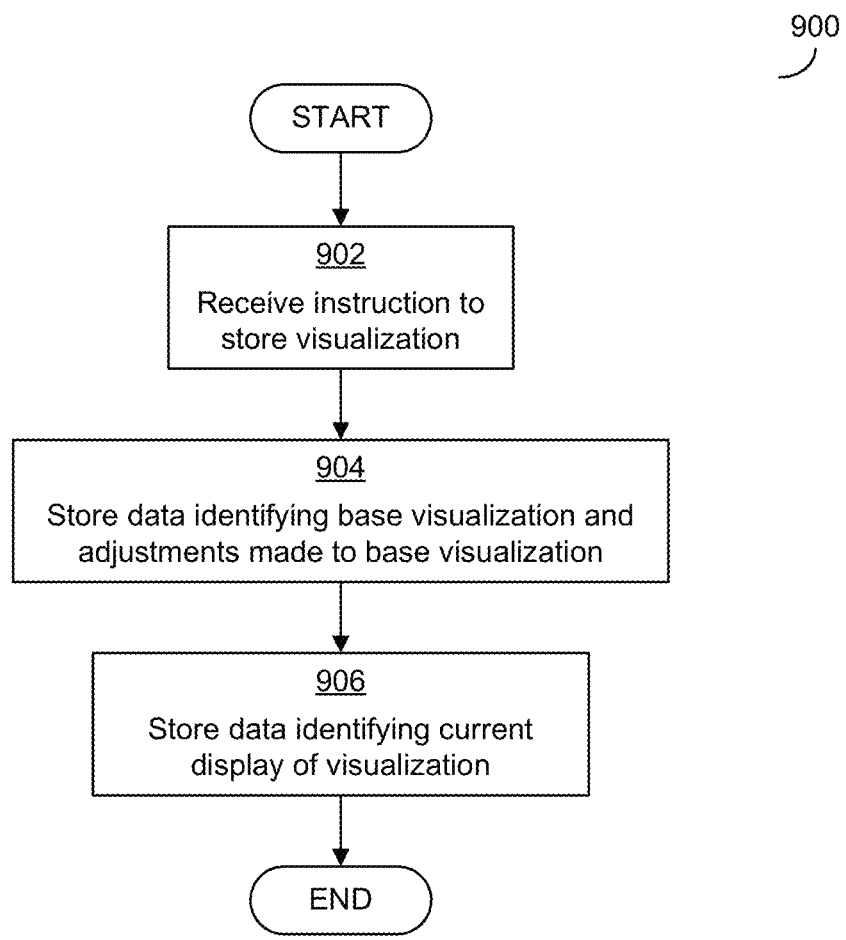
FIG. 9 is a flowchart of an exemplary process for storing information regarding an adjusted visualization.

Various techniques are described above for generating a visualization based on input describing an adjustment to be made to the visualization. In some embodiments, an adjusted visualization generated by a visualization facility may be stored by a visualization system, to enable subsequent retrieval and display of that adjusted visualization. FIG. 9 illustrates an example of a process that may be performed in some embodiments for storage of a visualization.

As discussed above in connection with FIG. 1B, in some embodiments it may be advantageous for all information connected to a patient's medical history to stay on a client device, or within the control of a user of a visualization system rather than of an operator or provider of the visualization system, in cases in which the two are different. For example, as discussed above in connection with FIG. 1B, in some cases one entity may provide base visualizations, predefined adjustments, and a visualization facility, and another entity may use those resources to create adjusted visualizations, including based on patient medical information. This division of functionality may be advantageous where the patient medical information includes sensitive information, as this division may enable creation of adjusted visualizations without transfer of the sensitive information to the entity that initially supplied the resources.

The process 900 of FIG. 9 may provide similar advantages, by enabling storage of information regarding an adjusted visualization without storage of sensitive data by a party other than a medical provider. For example, an entity that operates a visualization facility to generate an adjusted visualization may further operate the visualization facility to perform the process 900 of FIG. 9 and store the adjusted visualization in its own data store.

The process 900 begins in block 902, in which a visualization facility receives an instruction to store a current adjusted visualization. In response, in block 904, the visualization facility accesses information describing a current adjusted visualization. The information describing the adjusted visualization may include information describing a base visualization that was adjusted to create the adjusted visualization, as well as a roster of one, two, or more adjustments that were made to produce the adjusted visualization. The information on the base visualization may identify the base visualization in any suitable manner, including by identifying the base visualization as one of the visualizations 102, 104 discussed above in connection with FIG. 1A. The information on the adjustments may include information that was input to the visualization facility to make the adjustments or information that was generated by the visualization facility in response to an input, or any other suitable information that may be stored to re-create the adjustments. By storing information on the base visualization and the one or more adjustments that were made, when this information is subsequently retrieved and processed, the identified adjustments may be repeated by the visualization facility to adjust the identified base visualization, and by doing so recreate the adjusted visualization. The accessed information is stored in block 906.

In addition, in some embodiments, in block 908 the visualization facility may additionally store information on a current display of the adjusted visualization. The information on the current display may include information identifying a current "view" of the visualization, such as a perspective from which the visualization is being viewed as currently shown in a display (which may be known as a camera angle), a current zoom level of the visualization, a position of a light source within the visualization (if applicable), or other information that regulates a manner of display of a visualization. By storing this information in block 906, when the visualization facility re-renders the adjusted visualization using the information stored in block 904, the facility may additionally tune the display of the re-rendered adjusted visualization to match a current display of the visualization at the time the instruction is received in block 902.

Once the information is stored in blocks 904, 906, the process 900 ends.

The example of FIG. 9 was discussed in connection with storing an identification of a base visualization as well as an identification of adjustments to be made. While some embodiments may operate in this manner, it should be appreciated that embodiments are not so limited. Rather than storing this information, in some embodiments graphics data or other information for an adjusted visualization may be stored. For example, the adjusted visualization may be stored as graphics data that, when provided to a graphics system of a computing device (e.g., a driver for a graphics card) can be output for display. The adjusted visualization may additionally or alternatively, in some embodiments, be stored as instructions for generating such graphics data, with the instructions set out using any suitable graphics instruction set, including according to a graphics library API (e.g., OpenGL, WebGL, etc.). The adjusted visualization may additionally or alternatively be stored, in some embodiments, as a hierarchy of data objects, similar to the hierarchy 102B described in detail above in connection with FIG. 1A, that include information on how to render one or more anatomical features. Embodiments are not limited to storing information on a visualization in any particular manner.

Techniques operating according to the principles described herein may be implemented in any suitable manner. Included in the discussion above are a series of flow charts showing the steps and acts of various processes that generate adjusted three-dimensional visualizations of anatomy. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 1006 of FIG. 10 described below (i.e., as a portion of a computing device 1000) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the exemplary computer system of FIG. 1A or 1B, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 10:
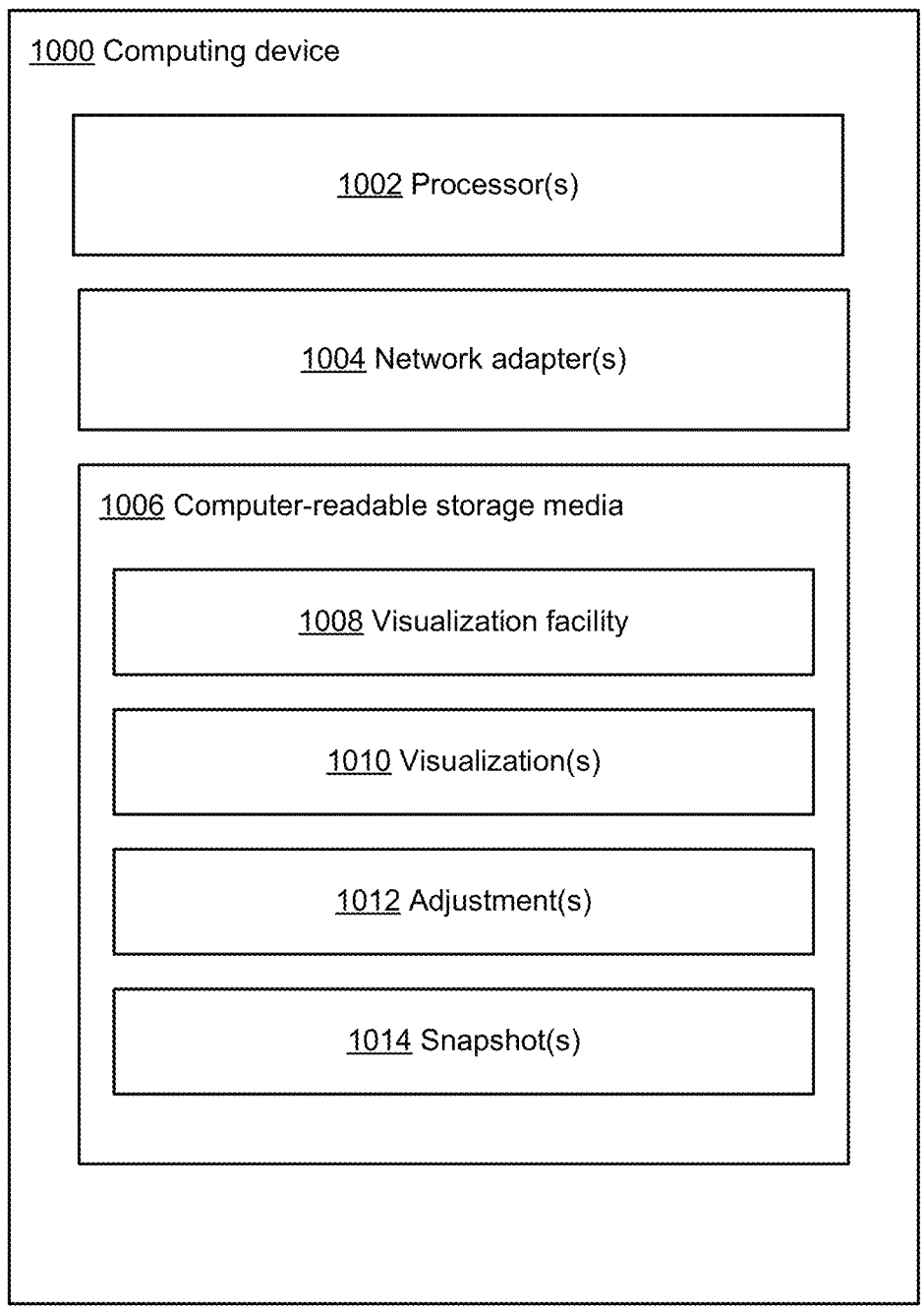
FIG. 10 is a block diagram of a computing device with which some embodiments may operate.

FIG. 10 illustrates one exemplary implementation of a computing device in the form of a computing device 1000 that may be used in a system implementing techniques described herein, although others are possible. It should be appreciated that FIG. 10 is intended neither to be a depiction of necessary components for a computing device to operate in accordance with the principles described herein, nor a comprehensive depiction.

Computing device 1000 may comprise at least one processor 1002, a network adapter 1004, and computer-readable storage media 1006. Computing device 1000 may be, for example, a desktop or laptop personal computer, a personal digital assistant (PDA), a smart mobile phone, a server, or any other suitable computing device. Network adapter 1004 may be any suitable hardware and/or software to enable the computing device 1000 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1006 may be adapted to store data to be processed and/or instructions to be executed by processor 1002. Processor 1002 enables processing of data and execution of instructions. The data and instructions may be stored on the computer-readable storage media 1006 and may, for example, enable communication between components of the computing device 1000.

The data and instructions stored on computer-readable storage media 1006 may comprise computer-executable instructions implementing techniques which operate according to the principles described herein. In the example of FIG. 10, computer-readable storage media 1006 stores computer-executable instructions implementing various facilities and storing various information as described above. Computer-readable storage media 1006 may store a visualization facility 1008 that may implement one or more of the techniques described above. The storage medium 1006 may additionally include information on one or more visualizations 1010, which may include information discussed in connection with visualizations 102, 104 of FIG. 1A. Information one or more predefined adjustments 1012 may also be stored, as discussed above in connection with predefined adjustments 106 of FIG. 1A, and one or more snapshots 1014 that are stored copies of generated adjusted visualizations, as discussed above in connection with FIG. 9.

While not illustrated in FIG. 10, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A method of operating a computing system to generate computer-readable data representing a three-dimensional visualization of at least a portion of anatomy of a human body, the method comprising:
   receiving, at least one server computing device from at least one client computing device and via at least one Application Programming Interface (API) call made by the at least one client computing device and via at least one network, a specification of an adjustment to be made to a base three-dimensional visualization of the at least the portion of the anatomy of the human body, wherein the specification of the adjustment comprises an identification of the adjustment to make and an indication of at least one anatomical feature of the human body to which the adjustment relates;
   wherein receiving the specification of an adjustment comprises receiving data in a format of a plurality of formats, wherein the data corresponds to the adjustment to make; determining a method to process the data based on the format of the data;
   processing the data; and identifying the adjustment to make;
   mapping, with at least one processor of the at least one server computing device, the indication of the at least one anatomical feature of the human body to one or more objects of a hierarchy of objects, wherein each object of the hierarchy of objects corresponds to one or more anatomical features of the human body and to one or more elements of the base three-dimensional visualization, wherein the one or more objects are related to one or more related objects via one or more connections;
   generating, with at least one processor of the at least one server computing device, an adjusted three-dimensional visualization of the at least the part of the anatomy of the human body by adjusting the one or more elements of the base three-dimensional visualization based at least in part on the adjustment, wherein the one or more elements of the base three-dimensional visualization that are adjusted correspond to the one or more objects that were mapped to the at least one anatomical feature indicated by the specification of the adjustment, and wherein the adjusted three-dimensional visualization includes the adjustment at the one or more elements that correspond to the one or more objects, wherein generating the adjusted three-dimensional visualization comprises distributing the information on how to render the feature to the one or more related objects; and
   communicating, as at least one response to the at least one API call made by the at least one client computing device and via the at least one network, the adjusted three-dimensional visualization of the at least the part of the anatomy of the human body from the at least one server computing device to the at least one client computing device.

2. The method of claim 1, wherein:
   the at least one server computing device is configured to receive the specification comprising the indication of the at least one anatomical feature in a plurality of formats; and
   the mapping comprises mapping from a format, of the plurality of formats, in which the indication of the at least one anatomical feature is specified to the hierarchy of objects.

3. The method of claim 2, wherein:
   the mapping comprises selecting a manner in which to perform a translation based on the format of the indication of the at least one anatomical feature.

4. The method of claim 1, wherein:
   receiving the specification comprising the indication of the at least one anatomical feature comprises receiving a specification comprising an identifier for the at least one anatomical feature in a first medical ontology; and
   mapping the indication to the one or more objects comprises mapping the identifier in the first medical ontology to a second medical ontology associated with the one or more objects.

5. The method of claim 4, wherein receiving the specification comprising the identifier for the at least one anatomical feature in the medical ontology comprises receiving an alphanumeric identifier in the first medical ontology.

6. The method of claim 4, wherein:
   receiving the specification comprising the identification of the adjustment to make and the identifier for the at least one anatomical feature in the medical ontology comprises receiving a code in the first medical ontology for a medical condition that affects one or more particular anatomical features; and
   mapping the indication to the one or more objects comprises identifying the one or more particular anatomical features from the code in the first medical ontology.

7. The method of claim 1, wherein:
   receiving the specification comprising the indication of the at least one anatomical feature comprises receiving a specification comprising an identifier for an anatomical system of the human body, the anatomical system comprising the at least one anatomical feature; and
   mapping the indication to the one or more objects comprises mapping the identifier for the anatomical system to the one or more objects that correspond to the at least one anatomical feature based on the identifier for the anatomical system.

8. The method of claim 7, wherein:
   the hierarchy of objects comprises a first node for the anatomical system and at least one second node, associated with the first node in the hierarchy and below the first node in the hierarchy, associated with the at least one anatomical feature, the at least one second node being the one or more objects; and
   mapping the identifier to the one or more objects comprises mapping the identifier to the first node.

9. The method of claim 1, wherein:
   receiving the specification comprising the indication of the at least one anatomical feature comprises receiving a specification comprising an identifier for a portion of an organ of the human body; and
   mapping the indication to the one or more objects comprises mapping the identifier for the portion to the one or more objects that correspond to the at least one anatomical feature.

10. The method of claim 1, wherein:
    receiving the specification comprising the indication of the at least one anatomical feature comprises receiving a specification comprising an identifier for a portion of an organ of the human body; and mapping the indication to the one or more objects comprises mapping the identifier for the portion to the one or more objects that correspond to the portion of the organ.

11. The method of claim 1, wherein:

receiving the specification comprising the indication of the at least one anatomical feature comprises receiving a specification comprising a coordinate in a coordinate system of a display of a visualization of the at least the portion of the anatomy; and mapping the indication to the one or more objects comprises identifying the at least one anatomical feature at least in part by determining an anatomical feature that corresponds to content of the visualization displayed at the coordinate.

12. The method of claim 11, wherein the coordinate of the coordinate system is a three-dimensional coordinate of a three-dimensional coordinate system.

13. The method of claim 1, wherein:

receiving the specification of the adjustment to make comprises receiving a specification of a medical condition to visualize in the adjusted three-dimensional visualization and an identification of one or more anatomical features affected by the medical condition; and generating the adjusted three-dimensional visualization comprises generating a three-dimensional visualization of the at least the portion of the anatomy of the human body with the medical condition.

14. The method of claim 13, wherein generating the three-dimensional visualization of the at least the portion of the anatomy of the human body with the medical condition comprises generating a three-dimensional visualization with the one or more elements that relate to the one or more anatomical features affected by the medical condition having at least one geometric modification as compared to the base three-dimensional visualization.

15. The method of claim 14, wherein:

the indication of the at least one anatomical feature indicates at least one organ affected by the medical condition and to be visualized with the medical condition;

the method further comprises retrieving data indicating how to visualize an effect of the medical condition on the at least one organ, wherein retrieving the data comprises retrieving from a data set of geometric modifications to be made to visualize each of a plurality of medical conditions, and where retrieving the data comprises retrieving the data based on the medical condition; and generating the three-dimensional visualization of the at least the portion of the human body with the medical condition comprises making at least one geometric modification to at least one geometric dimension of at least one model of the at least one organ in the base three-dimensional visualization based at least in part on the data.

16. The method of claim 15, wherein:

generating the adjusted three-dimensional visualization from the base three-dimensional visualization comprises generating an animated three-dimensional visualization;

the base three-dimensional visualization comprises information indicating a normal movement of the at least the portion of the anatomy of the human body; and making the at least one geometric modification comprises making at least one geometric modification to at least one geometric dimension of the base three-dimensional visualization that affects an animation of the adjusted three-dimensional visualization to reflect an abnormal movement of the at least the portion of the anatomy of the human body due to the medical condition.

17. The method of claim 15, wherein:

the base three-dimensional visualization comprises information indicating a normal appearance of the at least the portion of the anatomy of the human body; and making the at least one geometric modification comprises making at least one change to at least one geometric dimension of the base three-dimensional visualization to affect an appearance of the adjusted three-dimensional visualization to reflect an abnormal appearance of the at least the portion of the anatomy of the human body due to the medical condition.

18. The method of claim 14, wherein:

the specification of the adjustment is a first specification of a first adjustment to make, the indication of the at least one anatomical feature is a first indication of at least one first anatomical feature, and the medical condition is a first medical condition;

the method further comprises receiving, at the at least one server computing device via the at least one API call made by the at least one client computing device and via the at least one network, a second specification of a second adjustment to make to the base three-dimensional visualization of the at least the portion of the anatomy of the human body, wherein the second specification of the second adjustment comprises an identification of a second medical condition to visualize and a second indication of at least one anatomical feature of the human body to visualize with the second medical condition; and generating the adjusted three-dimensional visualization further comprises generating a three-dimensional visualization of the at least the portion of the anatomy of the human body with the second medical condition.

19. The method of claim 18, wherein:

the first indication for the first adjustment identifies a human organ to be visualized with the first medical condition, the human organ being included in the at least the portion of the anatomy of the human body;

the second indication for the second adjustment identifies that that second medical condition applies to an entirety of a human body;

generating the adjusted three-dimensional visualization comprises making at least one first geometric modification to the at least the portion of the anatomy in the base three-dimensional visualization to effect a visualization of the at least the portion of the anatomy with the first medical condition and making at least one second geometric modification to the at least the portion of the anatomy in the base three-dimensional visualization to effect a visualization of the at least the portion of the anatomy with the second medical condition.

20. The method of claim 19, wherein:

the first indication for the first adjustment identifies a human organ to be visualized with the first medical condition, the human organ being included in the at least the portion of the anatomy of the human body;

the second indication for the second adjustment identifies that that second medical condition applies to an entirety of a human body;

generating the adjusted three-dimensional visualization comprises making at least one first geometric modification to the at least the portion of the anatomy in the base three-dimensional visualization to effect a visualization of the at least the portion of the anatomy with the first medical condition and retrieving a three-dimensional visualization of a human body with the second medical condition to serve as the base three-dimensional visualization.

21. The method of claim 13, wherein:
the base three-dimensional visualization is a visualization from a plurality of three-dimensional visualizations, where the base three-dimensional visualization is a visualization of anatomy for a standard human body and one or more of the plurality of visualizations each correspond to anatomy of a human body with one or more medical conditions, each of the one or more of the plurality of visualizations comprising one or more geometric modifications as compared to the base three-dimensional visualization; and
adjusting the one or more elements of the base three-dimensional based at least in part on the adjustment comprises selecting a first three-dimensional visualization of the plurality of three-dimensional visualizations for use in generating the adjusted three-dimensional visualization, wherein selecting the first three-dimensional visualization of the plurality of three-dimensional visualizations comprises selecting based on the medical condition.

22. The method of claim 21, wherein selecting the first three-dimensional visualization of the plurality of three-dimensional visualizations for use in generating the adjusted three-dimensional visualization comprises, in response to the medical condition, selecting the first three-dimensional visualization of the plurality of three-dimensional visualizations to replace the base three-dimensional visualization.

23. The method of claim 1, wherein:
receiving the specification of the adjustment to make comprises receiving a specification of a label to display in the adjusted three-dimensional visualization and at least one anatomical feature with which to associate the label; and
generating the adjusted three-dimensional visualization comprises generating a three-dimensional visualization of the at least the portion of the anatomy of the human body with the label.

24. The method of claim 23, wherein receiving the specification of the label to display comprises receiving one or more of text, an image, or a video.

25. The method of claim 1, wherein:
receiving the specification of the adjustment to make comprises receiving a specification of at least one anatomical feature to omit from the at least the portion of the anatomy of the human body in the adjusted three-dimensional visualization, wherein the specification identifies the adjustment as an omission; and
generating the adjusted three-dimensional visualization comprises generating a three-dimensional visualization of the at least the portion of the anatomy of the human body without the at least one anatomical feature.

26. The method of claim 1, wherein receiving the specification of the adjustment to make comprises:
receiving a medical record identifying one or more attributes of a person; and
processing the medical record to determine the specification of the adjustment based at least in part on the one or more attributes of the person, wherein the specification of the adjustment comprises an indication of a manner in which the at least one anatomical feature is to be rendered within a user interface associated with the medical record.

27. The method of claim 1, wherein the adjusted three-dimensional visualization is output for display at the at least one client computing device.

28. The method of claim 27, wherein the adjusted three-dimensional visualization is output for display via a display screen of the at least one client computing device.

29. The method of claim 1, wherein the at least one client computing device is a mobile device.

30. The method of claim 1, further comprising:
generating a first three-dimensional visualization of the at least the portion of the anatomy of the human body; and
outputting, for display, the first three-dimensional visualization to the at least one client computing device,
wherein the receiving the specification and the generating the adjusted three-dimensional visualization are performed after the generating the first three-dimensional visualization and the outputting the first three-dimensional visualization for display.

31. The method of claim 1, further comprising:
wherein the determining a method to process the data based on the format of the data includes:
extracting, from the base three-dimensional visualization, information regarding a manner of rendering an anatomical feature, and
substituting the extracted information for corresponding information in the base three-dimensional visualization.

32. At least one non-transitory computer-readable storage medium having encoded thereon executable instructions that, when executed by at least one processor, cause the at least one processor to carry out a method of operating a computing system to generate computer-readable data representing a three-dimensional visualization of at least a portion of anatomy of a human body, the method comprising:
receiving, at least one server computing device from at least one client computing device and via at least one Application Programming Interface (API) call made by the at least one client computing device and via at least one network, a specification of an adjustment to be made to a base three-dimensional visualization of the at least the portion of the anatomy of the human body, wherein the specification of the adjustment comprises an identification of the adjustment to make and an indication of at least one anatomical feature of the human body to which the adjustment relates;
wherein receiving the specification of an adjustment comprises receiving data in a format of a plurality of formats, wherein the data corresponds to the adjustment to make; determining a method to process the data based on the format of the data;
processing the data; and identifying the adjustment to make;
mapping, with at least one processor of the at least one server computing device, the indication of the at least one anatomical feature of the human body to one or more objects of a hierarchy of objects, wherein each object of the hierarchy of objects corresponds to one or more anatomical features of the human body and to one or more elements of the base three-dimensional visualization, wherein the one or more objects are related to one or more related objects via one or more connections;

generating, with at least one processor of the at least one server computing device, an adjusted three-dimensional visualization of the at least the part of the anatomy of the human body by adjusting the one or more elements of the base three-dimensional visualization based at least in part on the adjustment, wherein the one or more elements of the base three-dimensional visualization that are adjusted correspond to the one or more objects that were mapped to the at least one anatomical feature indicated by the specification of the adjustment, and wherein the adjusted three-dimensional visualization includes the adjustment at the one or more elements that correspond to the one or more objects, wherein generating the adjusted three-dimensional visualization comprises distributing the information on how to render the feature to the one or more related objects; and communicating, as at least one response to the at least one API call made by the at least one client computing device and via the at least one network, the adjusted three-dimensional visualization of the at least the part of the anatomy of the human body from the at least one server computing device to the at least one client computing device.

33. A system comprising:

at least one server computing device comprising at least one first processor, and at least one data store storing a base three-dimensional visualization of at least a portion of anatomy of a human body; and at least one client computing device comprising at least one second processor, and at least one non-transitory computer-readable storage medium having encoded thereon executable instructions that, when executed by the at least one second processor, cause the at least one second processor to carry out a method comprising:

receiving, via at least one Application Programming Interface (API) call at the at least one client computing device and from at least one process executing on the at least one client computing device that makes the at least one API call, a specification of an adjustment to be made to the base three-dimensional visualization of the at least the portion of the anatomy of the human body, wherein the specification of the adjustment comprises an identification of the adjustment to make and an indication of at least one anatomical feature of the human body to which the adjustment relates;

wherein receiving the specification of an adjustment comprises receiving data in a format of a plurality of formats, wherein the data corresponds to the adjustment to make; determining a method to process the data based on the format of the data; processing the data; and identifying the adjustment to make;

mapping, with at least one second processor of the at least one client computing device, the indication of the at least one anatomical feature of the human body to one or more objects of a hierarchy of objects, wherein each object of the hierarchy of objects corresponds to one or more anatomical features of the human body and to one or more elements of the base three-dimensional visualization, wherein the one or more objects are related to one or more related objects via one or more connections; and generating, with at least one second processor of the at least one client computing device, an adjusted three-dimensional visualization of the at least the part of the anatomy of the human body, wherein generating an adjusted three-dimensional visualization comprises:

retrieving, by the at least one client computing device, the base three-dimensional visualization from the data store of the at least one server computing device, and adjusting, by the at least one client computing device, the one or more elements of the base three-dimensional visualization based at least in part on the adjustment, wherein the one or more elements of the base three-dimensional visualization that are adjusted correspond to the one or more objects that were mapped to the at least one anatomical feature indicated by the specification of the adjustment, and wherein the adjusted three-dimensional visualization includes the adjustment at the one or more elements that correspond to the one or more objects, wherein adjusting the one or more elements comprises distributing the information on how to render the feature to the one or more related objects.

* * * * *